(12) United States Patent  (10) Patent No.: US 8,073,805 B2
Yoo et al.  (45) Date of Patent: Dec. 6, 2011

(54) SENSORY TESTING DATA ANALYSIS BY CATEGORIES

(75) Inventors: Herb Yoo, Beaverton, OR (US); Alan W. Reichow, Beaverton, OR (US); Thomas R. Fortune, Jr., Aloha, OR (US); Matthew Genar Hilla, Portland, OR (US); Rick M. Rezinas, Portland, OR (US)

(73) Assignee: Nike, Inc., Beaverton, OR (US)

( * ) Notice: Subject to any disclaimer, the term of this patent is extended or adjusted under 35 U.S.C. 154(b) by 297 days.

(21) Appl. No.: 12/534,623

(22) Filed: Aug. 3, 2009

(65) Prior Publication Data

US 2010/0070453 A1 Mar. 18, 2010

Related U.S. Application Data

(63) Continuation-in-part of application No. 12/239,709, filed on Sep. 26, 2008.

(60) Provisional application No. 60/975,400, filed on Sep. 26, 2007.

(51) Int. Cl.
*G06N 5/00* (2006.01)
(52) U.S. Cl. .......................................... 706/54; 706/45
(58) Field of Classification Search .................... 706/54, 706/45
See application file for complete search history.

(56) References Cited

U.S. PATENT DOCUMENTS

| | | | |
|---|---|---|---|
| 3,861,790 A | 1/1975 | Tamura | |
| 5,050,982 A | 9/1991 | Meissner | |
| 5,478,239 A | 12/1995 | Fuerst | |
| 5,692,501 A | 12/1997 | Minturn | |
| 6,755,525 B2 | 6/2004 | Reichow | |
| 6,811,258 B1 | 11/2004 | Grant | |
| 6,893,127 B2 | 5/2005 | Reichow | |
| 7,073,208 B2 | 7/2006 | Penque | |
| 2004/0171460 A1 | 9/2004 | Park | |
| 2007/0282912 A1 | 12/2007 | Reiner | |
| 2008/0015819 A1 | 1/2008 | Sayre et al. | |
| 2009/0192361 A1 | 7/2009 | Yoo et al. | |

OTHER PUBLICATIONS

Rosenfeld, et al., Clinical practice guideline: Acute otitis externa, Otolaryngology-Head and Neck Surgery, 2006, v. 134, pp. S4-S23.*
Sanyal, Survey, Analysis and Correlation of Medical Students' Thinking, Learning and Type Preferences and Stress Levels—Relevance to Learning, Master's Thesis, University of Bath, 2007, pp. 1-213.*

(Continued)

*Primary Examiner* — Wilbert L Starks
(74) *Attorney, Agent, or Firm* — Shook, Hardy & Bacon L.L.P.

(57) ABSTRACT

This invention is related to systems and methods of analyzing sensory ability data. One embodiment of the present invention includes a method comprising the steps of receiving data from a remote location. The data is comprised of sensory ability data and demographic data associated with a subject. The data may then be stored. Further, the method includes identifying a potential evaluation level associated with the subject. The evaluation level is identified, at least in part, utilizing a sports tree function. The method also includes retrieving peer data associated with the potential evaluation level. Additionally, the method includes determining when the peer data is statistically powerful for use in generating a comparative profile of the sensory ability data associated with the subject. Additional embodiments develop training programs based on one or more training program functions.

20 Claims, 14 Drawing Sheets

OTHER PUBLICATIONS

Reichow, et al., "Introduction to Behavioral Optometry", Sports Vision, 1993, 75 pages, Optometric Extension Program Foundation, United States.

Ferreira, "An Overview of Research in Sports Vision: its History and an Optometric Perspective", The South African Optometrist, Dec. 2003, pp. 142-149, vol. 62, No. 4, Auckland Park, South Africa.

Coffey, et al., "Visual Performance Enhancement in Sports Optometry", Sports Vision 1995, pp. 158-177, Butterworth-Heinermann, United States.

Cardall, "Contact Lenses in Sport: a General Overview", Optician, Jan. 13, 2006, pp. 22-25, vol. 231, No. 6034, United States.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Koenig, "Practicing Perception: Eyes Can Be Trained to be More Effective", USA Today Baseball Weekly, 1996, 3 pages, United States.

Coffey, et al., "Optometric Evaluation of the Elite Athlete," Problems in Optometry, Mar. 1990, pp. 32-59, vol. 2, No. 1, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

International Search Report and Written Opinion, International Application PCT/US2010/044255, 15 pages.

\* cited by examiner

| | | DYNAMIC SPORTS | | | |
|---|---|---|---|---|---|
| 500 → | | 1-24% | 25-49% | 50-74% | 75-99% |
| 522 { 1 | SKILL TEST 1 ~ 514 | | | | |
| 2 | SKILL TEST 2 | | | | |
| 3 | SKILL TEST 3 | | | | |
| 4 | SKILL TEST 4 | 1 | 2 | 5 | 7 |
| 5 | SKILL TEST 5 | | | | |
| 6 | SKILL TEST 6 | 526 | 528 | 534 | 538 |
| 7 | SKILL TEST 7 | | | | |
| 8 | SKILL TEST 8 ~ 516 | | | | |
| 524 { 9 | SKILL TEST 9 ~ 518 | | | | |
| 10 | SKILL TEST 10 | | | | |
| 11 | SKILL TEST 11 | | | | |
| 12 | SKILL TEST 12 | 3 | 4 | 6 | 8 |
| 13 | SKILL TEST 13 | 530 | 532 | 536 | 540 |
| 14 | SKILL TEST 14 | | | | |
| 15 | SKILL TEST 15 ~ 520 | | | | |
| | 502  504 | 506 | 508 | 510 | 512 |

*FIG. 5A.*

NON-DYNAMIC SPORTS

| | | | 1-24% | 25-49% | 50-74% | 75-99% |
|---|---|---|---|---|---|---|
| 552 | 1 | SKILL TEST 1 | 1 | 2 | 5 | 7 |
| | 2 | SKILL TEST 2 | | | | |
| | 3 | SKILL TEST 7 | | | | |
| | 4 | SKILL TEST 8 | | | | |
| | 5 | SKILL TEST 4 | | | | |
| | 6 | SKILL TEST 6 | | | | |
| | 7 | SKILL TEST 5 | | | | |
| | 8 | SKILL TEST 14 | | | | |
| 554 | 9 | SKILL TEST 15 | 3 | 4 | 6 | 8 |
| | 11 | SKILL TEST 13 | | | | |
| | 13 | SKILL TEST 11 | | | | |
| | 14 | SKILL TEST 3 | | | | |
| | 15 | SKILL TEST 9 | | | | |

SENSORY TESTING DATA ANALYSIS BY CATEGORIES

This application is a Continuation-in-Part of U.S. patent application Ser. No. 12/239,709 filed Sep. 26, 2008, which claims the benefit of priority of U.S. Provisional Patent Application 60/975,400, filed Sep. 26, 2007, all of which is incorporated by reference in their entirety herein.

TECHNICAL FIELD

The present invention relates generally to the testing, training, or analysis of the sensory abilities of individuals. More particularly, the present invention relates to the remote analysis of an individual's sensory ability.

BACKGROUND

One skilled in the art of sensory evaluation will be aware of a large number of sensory tests that may be performed to determine strengths and weaknesses of an individual's sensory abilities. Typically, such tests are applied to determine whether an individual may benefit from some form of sensory correction and/or training and, if so, what type and degree of sensory correction and/or training may be desirable. One skilled in the art will further realize that numerous activities, particularly competitive athletics, place particularized demands upon the sensory abilities of an individual.

SUMMARY

The present invention provides systems and methods of testing a subject's sensory ability at a remote location and analyzing the resulting sensory testing data at a central location. More particularly, a method in accordance with the present invention may receive data from a remote location. The data is comprised of sensory ability data and demographic data associated with a subject. The data may then be stored. Further, the method may include identifying a potential evaluation level associated with the subject. The evaluation level is identified, at least in part, utilizing a sports tree function. The method may also include retrieving peer data associated with the potential evaluation level. Additionally, the method may include determining when the peer data is statistically powerful for use in generating a comparative profile of the sensory ability data associated with the subject.

It should be noted that this Summary is provided to generally introduce the reader to one or more select concepts described below in the Detailed Description in a simplified form. This Summary is not intended to identify key assessment and/or required features of the claimed subject matter, nor is it intended to be used as an aid in determining the scope of the claimed subject matter.

BRIEF DESCRIPTION OF THE DRAWINGS

The present invention is described in detail below with reference to the attached drawing figures, which are incorporated by reference herein and wherein:

FIG. 5A illustrates a dynamic sport training program function in accordance with an exemplary embodiment of the present invention;

FIG. 5B illustrates a non-dynamic sport training program function in accordance with an exemplary embodiment of the present invention;

DETAILED DESCRIPTION

Figure 1:
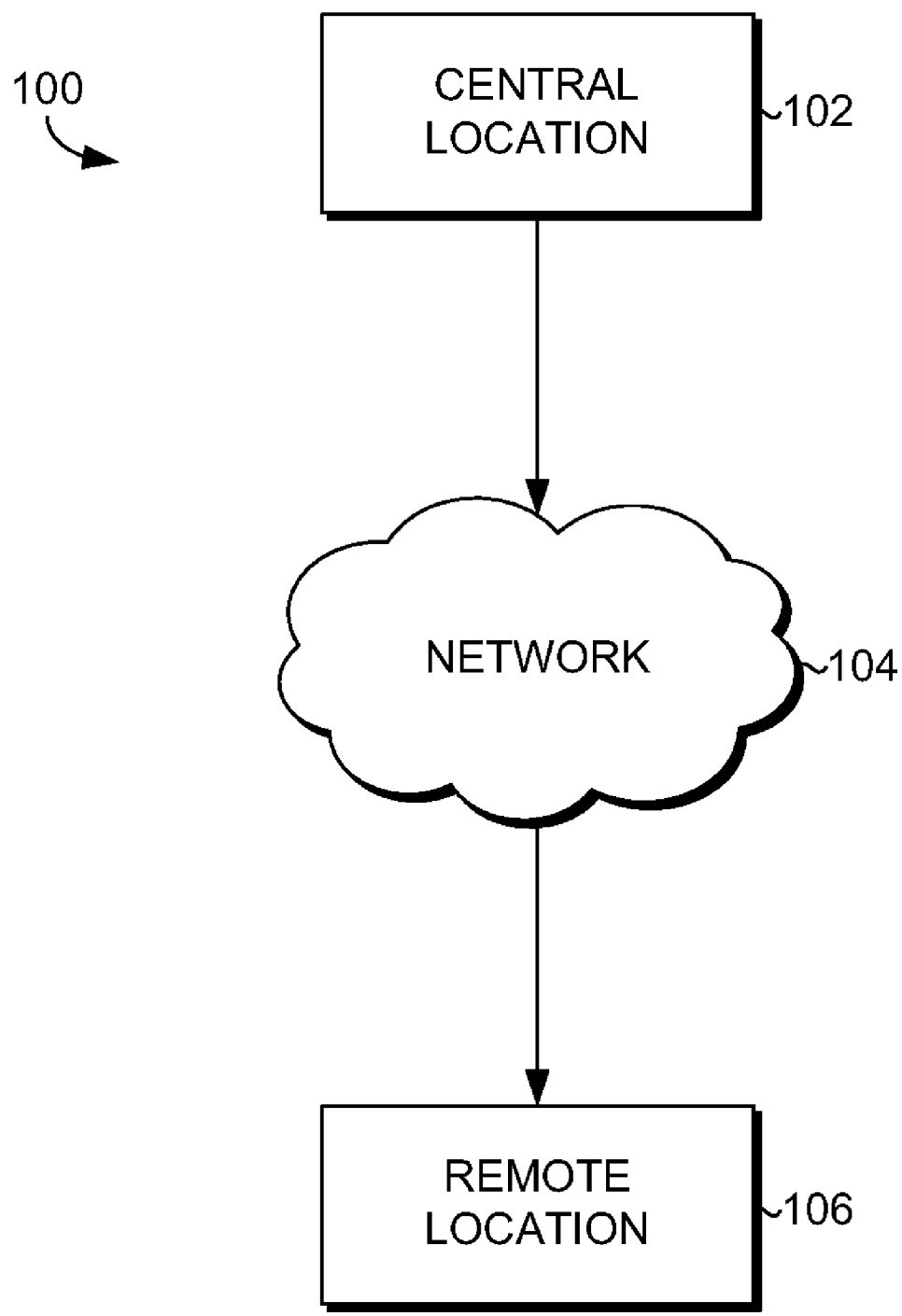
FIG. 1 illustrates a system in accordance with embodiments of the present invention.

The subject matter of embodiments of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Embodiments of the present invention relate to systems, methods, and computer storage media for receiving data from a remote location. The data is comprised of sensory ability data and demographic data associated with a subject. The data may then be stored. Further, the method may include identifying a potential evaluation level associated with the subject. The evaluation level is identified, at least in part, utilizing a sports tree function. The method may also include retrieving peer data associated with the potential evaluation level. Additionally, the method may include determining when the peer data is statistically powerful for use in generating a comparative profile of the sensory ability data associated with the subject.

A second method in accordance with the present invention may comprise identifying a first evaluation level associated with the subject. The evaluation level is identified, at least in part, utilizing a sports tree function. The sports tree function is comprised of a hierarchical structure that represents potential evaluation levels based on one or more traits of the subject. The method may also include retrieving peer data associated with the first evaluation level. The method may further include determining that the peer data associated with the first evaluation level is not statistically powerful for use in generating a comparative profile of the sensory ability data associated with the subject. The method may also include identifying a second evaluation level utilizing the sports tree function. The second evaluation level is higher on the hierarchical structure of the sports tree function. The method may additionally include retrieving peer data associated with the second evaluation level. The method may also include determining the peer data associated with the second evaluation level is statistically powerful for use in generating a comparative profile of the sensory ability data associated with the subject. Further, the method may include analyzing sensory data associated with the subject to generate a sensory ability assessment. The method may also include generating the sensory ability assessment.

A third method may be comprised of receiving demographic data of the subject and storing the demographic data. The method may also be comprised of receiving sensory data of the subject; the sensory data is collected at a remote location. The sensory data is comprised of one or more sensory evaluation metrics. The method may also include storing the sensory data in association with the demographic data. Additionally, the method may include receiving remote information. The remote information includes information related to the collection of the sensory data. The method may also include storing the remote information in association with the sensory data. Further, the method may include identifying an evaluation level that includes statistically powerful peer data. The peer data is comprised of sensory data from a plurality of other subjects. The method also includes analyzing the one or more sensory evaluation metrics of the subject's sensory data in relation to the peer data to generate a comparative profile of the subject's sensory ability. The method may additionally include generating the assessment of the subject's sensory ability. The method may also include storing the assessment in association with the demographic data. Further, the method may include communicating the assessment to the remote location. The method also may include developing a sensory training program for the subject utilizing a training program function. Additionally, the method may include storing the training program in association with the demographic data. The method may also include communicating the sensory training program to the remote location.

The present invention allows testing, data collection, and/or training to occur at a remote location different from the location where the analysis or assessment is performed and the training plan is developed. In accordance with this invention, sensory ability testing may occur at one or more remote locations, while the analysis of the testing data and development of the training plan occurs at a central location. The central location may analyze the data, and further may have the capability to access a network, such as the Internet, in order to receive data from the one or more remote locations. Additionally, it is contemplated that a remote location and a central location may be physically located within close proximity of one another (e.g., same physical unit, same network, same building, same city). Similarly, it is further contemplated that the testing, training, analysis, and/or development of a training plan may be accomplished at the remote location and/or the central location, either individually or in combination. Therefore, in an exemplary embodiment, functionality described herein may be accomplished at either, or both, a remote location and/or a central location. In yet another exemplary embodiment, a remote location is any location other than the central location, where testing may occur (e.g., a college athlete might undergo testing at their college's athletic facilities), and includes the capability to perform sensory ability testing and to access a network in order to transfer testing data to the central location.

The present invention is not limited to specified activities occurring at either a remote location and/or a central location. For example, in an embodiment of the present invention, testing, training, data collection, analysis, and development of a training plan may occur at one or more remote locations. Additionally, a central location may serve as a repository of data that is provided to and collected from the one or more remote locations. The central location may therefore facilitate the various activities occurring at the one or more remote locations. In an exemplary embodiment, an athletic training facility (i.e., remote location) where various activities (e.g., testing, data collection, training, analysis, and development of a training plan) are performed, accesses or receives additional information/data from a central location to complete at least some of the activities. For example, the central location may provide statistically powerful data that is utilized when analyzing sensory data of a subject. In an additional exemplary embodiment, the present invention performs activities that are less likely to compromise proprietary information (e.g., testing, training, and data collection) at a remote location, while activities that are desired to have a higher level of confidentiality (e.g., analysis, development of a training plan, development of a comparative profile) are performed at a central location.

Sensory testing gathers data on a subject's current sensory ability. Sensory ability may refer to a subject's sensory ability, perceptual ability, cognitive ability, visual ability, auditory ability, etc. The specific tests administered to a subject will vary depending on the individual's ability, desired activity, and competitive level. Using such tests, it may be determined during the assessment that the individual has a particular weakness and/or strength in a different aspect of his sensory ability. Given this weakness, a training program may be created to train the individual on that weakness. For example, if an individual's saccadic and peripheral sensory ability is weak, various baseline measurements will be analyzed during the assessment to determine such a weakness.

An individual's particularized activity may play a role in the specific tests administered. For example, an individual that participates in baseball will likely utilize different sensory skills than a soccer player, and therefore those two individuals will benefit from different sensory training plans and thus may undergo different sensory tests, although certain core tests might be used in each.

Additionally, the competitive level of the individual may lead to alterations in testing and training plans, so individuals may be assigned a specific evaluation level prior to testing. For instance, if the desired activity is some type of sport, a high-school athlete may be tested using a different evaluation level and thus receive a different training program than a college-level athlete, and a college-level athlete may be tested using a different evaluation level than a professional-level athlete. Typically, the higher the elevation level of the individual the more tests they may undergo.

Generally, the data collected from each subject may include demographic information, static sensory data, dynamic sensory data, and, optionally, health data. Demographic information may include the individual's name, gender, primary activity, evaluation level, and the like. Static sensory data may include, for example, measurements of the individual's static visual acuity, contrast sensitivity, depth perception, etc. Dynamic sensory data may include eye-hand coordination, dynamic visual acuity, split attention, eye-body coordination, dynamic tracking, etc. Examples of health data may include the dates of the previous examinations, gender, weight, etc. Once the testing has occurred, the data may be reviewed (e.g., by the trainer administering the testing) to verify the data prior to transferring the data to a central location. That is, the data may receive an initial check for obvious errors in case more testing is required.

Once the data is acquired from testing, it may then be collected. Testing data may be collected using various methods. By way of example, but not limitation, data may be collected in an electronic format by entering the data into a spreadsheet. Collection may occur indirectly, where an individual (e.g., a trainer) inputs the data using an input device, or directly, where the testing device automatically puts the data into a format to transfer the data. In another embodiment, the data may be collected by entering the testing data on a web portal that resides on a network. Again, in embodiments using a web portal, the data may be collected or entered directly or indirectly. Any type of computing device may be used in connection with one or more embodiments of the present invention. Exemplary computing devices include hand-held devices, consumer electronics, general-purpose computers, specialty-computing devices, and the like.

After the data has been collected, the data may be transferred to a central location for analysis. Various methods may be utilized to transfer the testing data to a central location. For example, the data may be collected in an electronic format, and thus the transfer of data may occur electronically. If, for example, the data has been collected on a spreadsheet, the spreadsheet containing the testing data may be transferred via email over the network to the central location. Alternatively, where the data has been collected in a web portal, the central location may access the web portal to retrieve the testing data.

The present invention may also provide for automatic collection and/or automatic transfer of testing data from one or more remote locations to a central location. In these embodiments, the various testing devices may have the capability to collect and/or transfer the testing data. Examples of such testing devices include eye-movement monitors, touch screens, display devices, input devices, corneal analyzers, etc. Thus, the device may measure an aspect of the individual's sensory ability and automatically collect the testing data in specified format. Further, the testing devices may have the capability of directly connecting to a network, which would allow the device to measure the data during the sensory ability tests, and automatically send the data to the central location to be analyzed, rather than first collecting the data before sending it to a central location.

Once the sensory ability data of an individual has been transferred to a central location, this data may be analyzed. Analysis of this data may be used to create a specific sensory training plan for the subject. Such analysis may occur manually by an administrator at the central location who might receive the testing data, interpret the data, and create a training plan based on their personal expertise. Alternatively, analysis may occur automatically. That is, the process may be automated where the data may be analyzed by, for example, a computing device.

Embodiments of the present invention may be embodied as, among other things: a method, system, or set of instructions embodied on one or more computer-readable media. Computer-readable media include both volatile and nonvolatile media, removable and nonremovable media, and contemplates media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

Turning now to the figures, FIG. 1 illustrates a sensory testing and/or training system 100 in accordance with an embodiment of the present invention. System 100 may include a central location 102, a network 104, and a remote location 106. While FIG. 1 only illustrates a single remote location 106, it is contemplated that system 100 may be comprised of two or more remote locations. For example, testing may occur at a first remote location, training may occur at a second remote location, and presentation of assessment results may occur at a third remote location. A remote location may comprise various components, although each remote location does not necessarily comprise the same components. The remote location 106 shown in FIG. 1 is merely an example of one suitable remote location and is not intended to suggest any limitation as to the scope of use or functionality of the present invention.

The various components, locations, and devices may communicate with each other via the network 104, which may include, without limitation, one or more local area networks (LANs) and/or wide area networks (WANs). In an exemplary embodiment, the network 104 is comprised of both wired and wireless networks. For example, the central location 102 may be connected to the network 104 utilizing a wired LAN while the remote location 106 may be connected to the network 104 by way of a wireless connection. Such networking environments are commonplace in offices, enterprise-wide computer networks, intranets, and the Internet.

Figure 2:
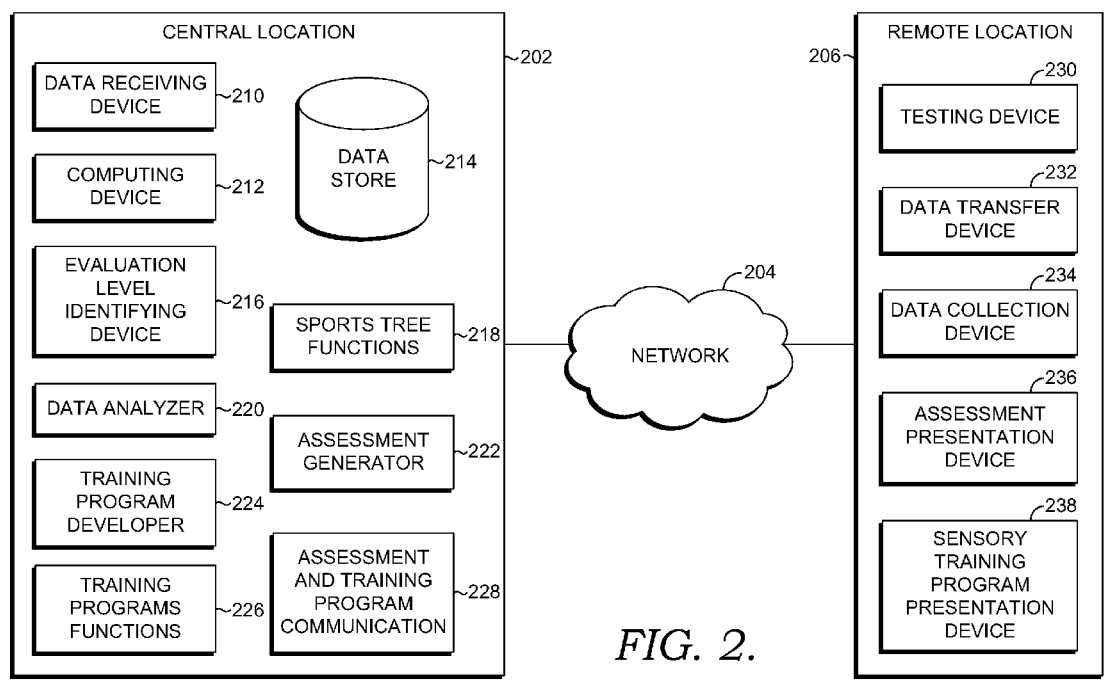
FIG. 2 illustrates a further system in accordance with embodiments of the present invention.

Turning to FIG. 2 that depicts a sensory testing and/or training system 200 in accordance with an embodiment of the present invention. The system 200 includes a central location 202, a network 204, and a remote location 206. The depiction of a single central location 202, a single network 204, and a single remote location 206 is not intended to be limiting as to the scope of the present invention; instead, the depicted configuration of system 200 is merely for demonstrative purposes.

The central location 202 is comprised of a data receiving device 210, a computing device 212, a data store 214, an evaluation level identifying device 216, sports tree functions 218, a data analyzer 220, an assessment generator 222, a training program developer 224, training program functions 226, and an assessment and training program communicator 228. In an exemplary embodiment, each of the various components and devices of the central location 202 are either directly or indirectly coupled to their own computing device or a shared computing device, such as the computing device 212. For example, the data store 214, which will be discussed in more detail below, is directly coupled to the computing device 212 in an exemplary embodiment. In an additional exemplary embodiment, the data store 214 is coupled to a computing device not depicted in FIG. 2, wherein the computing device functions as a controller of the data store to facilitate the accessing, writing, and reading of data to and from the data store 214.

The data-receiving device 210 is a data-receiving device that facilitates the communication of data to and from the central location 202. In an exemplary embodiment, the data-receiving device 210 is responsible for receiving data communicated from the remote location 206. In yet an additional embodiment, the data-receiving device 210 may be useable for receiving and requesting data from a remote data store that includes data useable for developing a training program and/or generating an assessment. The data-receiving device 210 may be functional to communicate in a protocol supported by the network 204. For example, the network 204 may utilize, at least in part, an Internet Protocol (IP) to facilitate the communication of data to and from the central location 202. Therefore, the data-receiving device, in this exemplary embodiment, is functional to receive data compatible with IP.

The computing device 212 is a computing device that includes a processor. In an exemplary embodiment, the computing device 212 is comprised of a processor and memory. For example, the computing device 212 may include one or more computer readable media that store computer-executable instructions for performing one or more methods. The computing device 212, in an exemplary embodiment controls one or more functions associated with the central location 202. For example, the computing device 212 may control the data-receiving device 210 to facilitate receiving data from the remote location 206. Further, the computing device 212 may provide one or more user interfaces that allow the various functions, components, and/or devices of the central location 202 to be manipulated by a user or a subject. In yet an additional embodiment, the computing device 212 is functional to present an assessment and/or a training program. For example, the computing device 212 may be further comprised of a display, printer, or other presentation peripheral that allows for a subject to view, hear, or otherwise receive the matter to be presented.

The data store 214 is a store of data. In an exemplary embodiment, the data store 214 is comprised of computer readable media. For example, the data store may include one or more data servers that include one or more hard drives that allow for the storage and retrieval of data. The data store 214 may store data associated with one or more subjects that participate in testing and/or training at the remote location 206. For example, the subject, the administrator, or another party may desire for data that is collected at the remote location 206 to be stored at a controlled location, such as the central location 202, to provide an additional level of confidentiality and/or redundancy to the data. Therefore, in an exemplary embodiment, the data store 214 is responsible for the storage of some or all data for the central location 202 and/or the remote location 206.

The data store 214 may store demographic data, sensory data, and remote location information. As previously discussed, demographic data is data that may describe one or more traits of a subject. For example, the demographic data may include, but not limited to, the subject's age, gender, race, height, weight, and information associated with determining an evaluation level (e.g., sport, sport class, position class, position). The sensory data, as also previously discussed, may include collected data results associated with one or more skill tests performed on or by a subject. For example, a subject may participate in a static visual acuity skill test that provides a result that is included in the sensory data associated with the subject. The remote location information includes information associated with collection of the sensory data. For example, a unique identifier (e.g., IP address, serial number, account number, physical location information) of the remote location 206 may comprise the remote location information. Additional information that may be included in the remote location information includes time and data information, testing center information, training center information, testing/training administrator information, and the like.

The evaluation level identifying device 216 is a device for identifying an evaluation level associated with a subject. For example, when analyzing a subject's sensory ability, it may be desirable to utilize an appropriate peer group. One method for identifying an appropriate peer group is to identify an appropriate evaluation level that encompasses only those peers necessary to have statistically powerful peer data to utilize in the analysis. For example, if a subject is a professional shortstop baseball player, analysis of the subject's sensory abilities should be done with respect to other professional baseball players, not compared to middle-school soccer players. In an exemplary embodiment, to identify an appropriate evaluation level, the sports tree functions 218 are used.

Figure 3A:
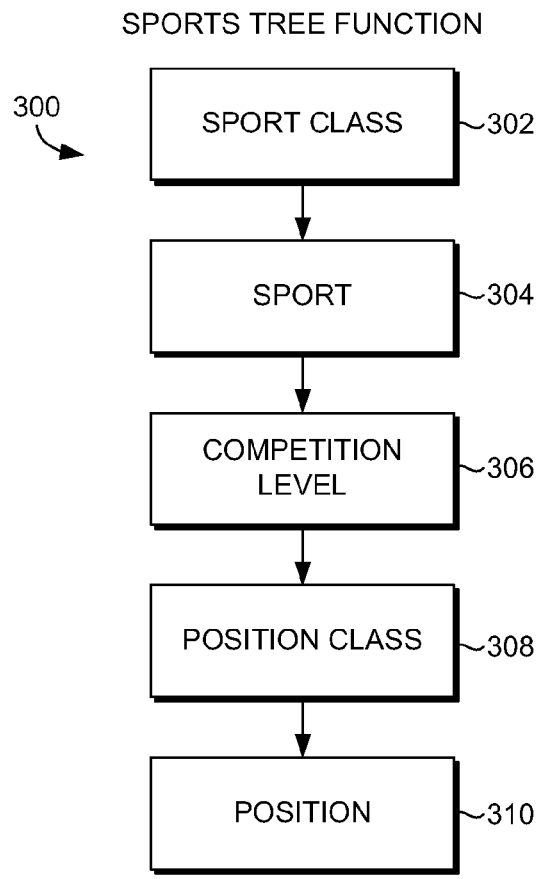
FIG. 3A illustrates a first simplified sports tree function in accordance with embodiments of the present invention.

Turning to FIG. 3A that depicts a first simplified sports tree function 300 in accordance with an embodiment of the present invention. The sports tree function 300 is merely an exemplary sports tree and not intended to be limiting as to the scope of the present invention. It is understood that one or more elements of the sports tree function 300 may be omitted, added, or referenced by alternative vernacular. The sports tree function 300 is comprised of the following levels, a sport class 302, a sport 304, a competition level 306, a position class 308, and a position 310.

The sports tree function 300 is a hierarchical structure that may be visualized as an inverted pyramid when viewed with respect to the breadth of scope represented by each layer. Stated differently, a finer level of detail is expected the lower down on the sports tree function 300. For example, a sport class 302 may include a classification of "pass and kick" that is comprised of football, rugby, and soccer in the sport level 304. Therefore, football and soccer are related in the exemplary sports tree function 300 as belonging to the same sport class 302. As a result, a finer level of detail is accomplished by moving down the sports tree function 300 from a sports class 302 to a particular sport 304. Each of the levels of the sports tree function 300 are discussed in greater detail in FIG. 4.

Figure 3B:
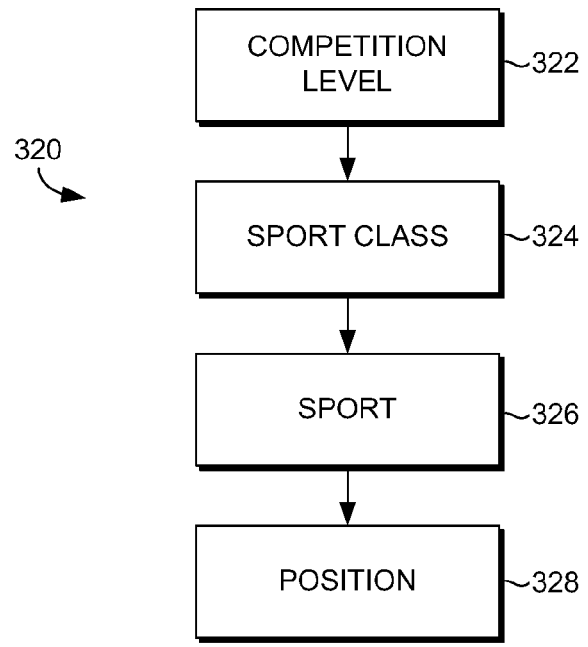
FIG. 3B illustrates a second simplified sports tree function in accordance with embodiments of the present invention.

Turning to FIG. 3B that illustrates a second simplified sports tree function 320 in accordance with an exemplary embodiment of the present invention. The sports tree function 320 is comprised of a competition level 322, a sport class 324, a sport level 326, and a position level 328. Similar to the sports tree 300 previously discussed with respect to FIG. 3A, the sports tree function 320 may include additional levels not illustrated. For example, a position class level is not illustrated as part of the sports tree function 320, but it is contemplated that additional levels may be incorporated in an exemplary embodiment of the present invention. Additionally, it is contemplated that one or more levels of the sports tree function 320 may be omitted or rearranged from the exemplary order illustrated. As a result, the sport tree function 320 is merely intended to be an exemplary sports tree function and not limiting as to the scope of the present invention.

Figure 4A:
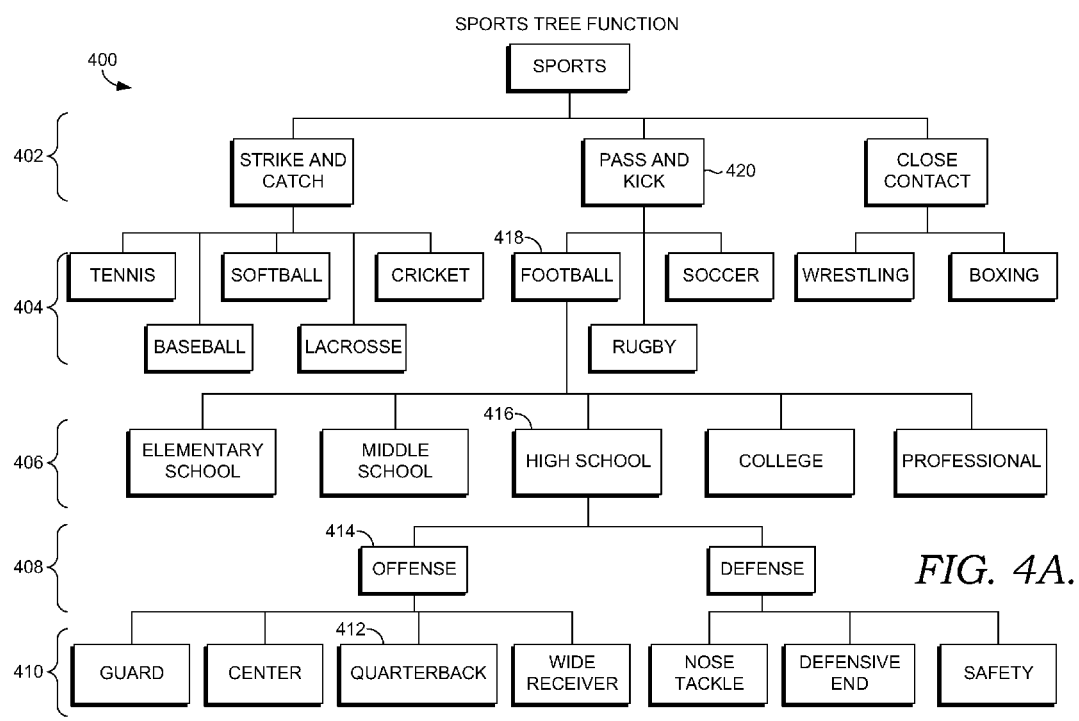
FIG. 4A illustrates a first sports tree function in accordance with an exemplary embodiment of the present invention.

The competition level 322 may include any number of classifications of competition levels. For example, competition levels may be classified as elementary school, middle school, high school, college, and professional as illustrated in FIG. 4A. Further, competition levels may also or alternatively be classified as youth, college, semi-professional, and professional as discussed later with respect to FIG. 4B. Additionally, the competition levels may be classified as any combination of competitive ranges. As a result, the competition level 322 may include any level of granularity required to achieve the results desired. For example, only one level of competition may be utilized or higher level of granularity may be utilized to provide greater classification.

The sports class 324 may be similar in concept to the sports class 302 previously discussed with respect to FIG. 3A. In an exemplary embodiment, as discussed in more detail with respect to FIG. 4B, the sports class 324 includes a small target dynamic classification, a large target dynamic classification, a target non-dynamic classification, and a non-target dynamic classification. The sport level 326 may be similar in concept to the sport 304 previously discussed with respect to FIG. 3A. In an exemplary embodiment, the sport level 326 is a hierarchical level of the sports tree 320 that identifies a particular sporting activity associated with a user. For example, sport level 326 may include at least hockey, baseball, basketball, football, volleyball, golf, shooting, boxing, snowboarding, and cheerleading. The position level of the sports tree 320 may be similar in concept to the position level 310 previously discussed with respect to FIG. 3A. For example, the position level 328 may include one or more particular positions of one or more sports of the sport level 326. It is contemplated that not all sports of the sport level 326 have associated positions at the position level 328.

Turning to FIG. 4A that illustrates a first sports tree function 400 in accordance with an exemplary embodiment of the present invention. The sports tree function 400 includes multiple levels similar to those of sports tree function 300 of FIG. 3A. The levels include a sports class level 402, a sport level 404, a competition level 406, a position class level 408, and a position level 410.

The sports class level 402 is a level that includes one or more classes of sports that may be associated based on similarities in activities, conditions, equipment, and/or requirements. For example, several nonlimiting sport classes of the sports class 402 include "Strike and Catch" class, a "Pass and Kick" class 420, and a "Close Contact" class. Therefore, in this example the classes are created based, at least in part, on the similarities in activities and conditions associated with underlying sports identified in the sports level 404.

For example, at the sports class level 402, the Pass and Kick class 420 includes a football sport 418, a rugby sport, and a soccer sport at the sport 404 level. Therefore, the Pass and Kick class 420 is a broader classification of each of football 418, rugby, and soccer. Continuing down on the hierarchical tree of the sports tree function 400, football 418 includes the following exemplary competition levels 406, elementary school, middle school, high school 416, college, and professional. In an exemplary embodiment, each sport of the sport class 404 includes competition levels appropriate to the particular sport. For example, if additional competition levels, such a minor league, club team, or the like are commonly associated with a given sport, those competition levels may supplement and/or substitute one or more levels of the competition level 406.

Continuing down the hierarchical structure of the sports tree function 400, the position class level 408 includes one or more classifications for each of the competition levels of a particular sport. For example, the position class level 408 includes an offense position class 414 and a defense position class. Therefore, in order to further refine an evaluation level, it may be advantageous to associate athletes from a particular position class together. For example, offense position class 414 players of a football team may utilize different sensory abilities than a defensive position class football player. As a result, it may be advantageous to compare an offensive player to another offensive player rather than football players in general. Similar to previous discussions, each competition class of the competition class level 406 may include tailored position classes in the position class level 408. For example, middle school baseball may include position classes for outfield, infield, and batting. Professional baseball may include left infield (e.g., third base, shortstop), right infield (e.g., second base, first base), outfield, etc. Even though both are classified as a sport of baseball, each level of competition may require a greater degree of granularity to achieve desirable analysis. Continuing down the hierarchical structure of the sports tree function 400, the position level 410 includes one or more positions for a particular position class. For example, positions of high-school football on the offense may include a right guard, a center, a quarterback 412, and a wide receiver. The position level 410 is a finer level of granularity of the position class.

The sports tree function 400 is merely an exemplary illustration of a sports tree function and is not intended to be limiting as to the scope of the present invention. Particular sport classes, sports, competition levels, position classes, and sports have been explicitly identified in this exemplary embodiment; however, additional embodiments are contemplated. For example, one or more levels may be omitted from the sports tree. Additionally, one or more levels may be included in the sports tree function to provide a greater degree of granularity control. Therefore, the sports tree function 400 provides an exemplary, nonlimiting, embodiment of a sports tree function.

In an exemplary embodiment, an evaluation level is identified for a subject utilizing the sports tree function 400. More than one evaluation level may be required depending, in an embodiment, on the quality of data associated with the assigned evaluation level. For example, if statistically powerful peer data is not available at a particular evaluation level, a broader evaluation level may be used to include additional peer data that may result in the cumulative peer data achieving a statistical power level. Statistically powerful data is data that allows for an assessment to be completed that achieves a predefined level of confidence. In an exemplary embodiment, a particular number of data points (e.g., data associated with peer subjects) are required before the peer data is considered to be statistically powerful. For example, 30 data points may be required before peer data is considered to be statistically powerful. Therefore, stated differently, peer data is considered statistically powerful when a predefined sample size threshold is achieved and/or exceeded.

When peer data is determined to not be statistically powerful, the evaluation level is increased (i.e., made broader in scope) to incorporate additional peer data. For example, a subject that is originally identified as having an evaluation level associated with quarterback 412 because the subject is a football player on a high-school team that plays offense and is a quarterback. However, if the peer data associated with the quarterback 412 evaluation level is not statistically powerful, then the subject may be identified with the evaluation level associated with offense 414. In this example, the broader evaluation level associated with offense 414 may incorporate additional peer data of high-school football guards, centers, and wide receivers. With the potential increase in peer data, a statistically powerful peer data pool may be achieved for use in assessing the subject's sensory data.

Demographic data may be used in combination with a sports tree function to identify an evaluation level of a subject. For example, demographic data associated with the subject may be accessed to identify a sport class, sport, competition level, position class, or position of the subject that may be utilized as input for a sports tree function. Additional information that may be used includes the subjects dominate eye, hand, or other factors that can be utilized to provide a finer refinement of the evaluation level.

Figure 4B:
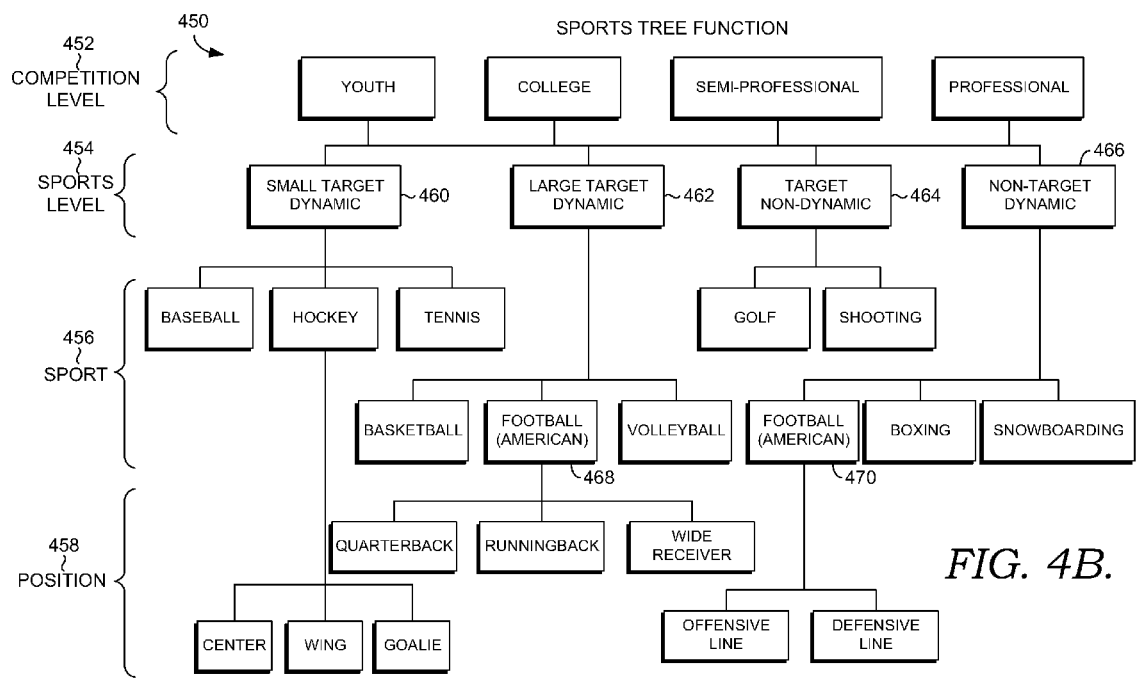
FIG. 4B illustrates a second sports tree function in accordance with an exemplary embodiment of the present invention.

Turning to FIG. 4B that illustrates a second sports tree function 450 in accordance with an exemplary embodiment of the present invention. The sports tree function 450 includes multiple levels similar to those of sports tree function 320 of FIG. 3B. The levels include a competition level 452, a sport class 454, a sport level 456, and a position level 458. The sports tree 450 may be similar in concept to the features discussed with respect to the sports tree function 400 of FIG. 4A.

The sports tree function 450 is merely an exemplary illustration of a sports tree function and is not intended to be limiting as to the scope of the present invention. Particular competition levels, sport classes, sports, and positions have been explicitly identified in this exemplary embodiment; however, additional embodiments are contemplated. For example, one or more levels may be omitted from the sports tree. Additionally, one or more levels may be included in the sports tree function to provide a greater degree of granularity control. For example, a position class level may be inserted between the sport level 456 and the position level 458. Therefore, the sports tree function 450 provides an exemplary, nonlimiting, embodiment of a sports tree function.

The competition level 452 includes a plurality of classifications that identify a level of competition at which a particular user is to be evaluated. In an exemplary embodiment, a user is evaluated at a competition level commensurate with the competition level at which the user competes. For example, a high school baseball player may be classified in a youth competition level. However, in an additional embodiment, a high school baseball player may desire to be evaluated and consequently tested and/or trained relative to a college or professional competition level classification. Therefore, the competition level for a particular user may change for a variety of circumstances. For example, the competition level of a user may be established at the level at which the user competes for testing purposes but may be established at a higher (e.g., more competitive) level for training purposes. Examples of competition level 452 classifications include youth, college, semi-professional, and professional. It is understood, as discussed with respect to FIG. 3B, that one or more additional categories may be added to increase the granularity or level of detail associated with the sports tree function 450. Similarly, one or more of the categories may be omitted to reduce the level of detail associated with the sports tree function 450.

The sport class 454 is a classification of various sports. In an exemplary embodiment, the sport class 454 may be similar in concept to the sport class 402 previously discussed with respect to FIG. 4A. As illustrated, the sport class 454 includes a small target dynamic classification 460, a large target dynamic classification 462, a target non-dynamic classification 464, and a non-target dynamic classification 466. In an exemplary embodiment, the sport class 454 includes categories separated based on target object characteristics. For example, the small target dynamic classification 460 may include all sports that utilize a target object with a perceived volume equal to or less than a softball. Examples include badminton, baseball, cricket, handball, hockey, lacrosse, racquetball, softball, table tennis, and tennis. The large target dynamic classification 462 may include all sports that utilize a target with a perceived volume greater than that of a softball. Examples include basketball, American football, global football (e.g., soccer), rugby, volleyball, and water polo. Target non-dynamic classification 464 may include sports that utilize a target, but the target is not dynamic at the point of a user's concern. Examples may include golf, archery, and biathlon shooting. Non-target dynamic classification 466 may include sports that require dynamic sensory skills, but the sport lacks a particular target object of focus. Examples may include, boxing, cheerleading, cycling, dance, diving, fencing, figure skating, gymnastics, martial arts, rowing, running, skateboarding, skiing, snowboarding, swimming, track and field, triathlon, and wrestling.

In an exemplary embodiment, a particular sport may be associated with more than one sport class. For example, American football may be associated with both large target dynamic classification 462 and non-target dynamic classification 466. In this example, American football 468 may include a variety of positions that require different sensory skills. Players whose primary purpose is to work with a football (e.g., handle a football, seek a football) may be associated with the large target dynamic classification 462. American football 470 players whose primary purpose is to interact with additional players (e.g., lineman) may be associated with the non-target dynamic classification 466. Therefore, it is contemplated that a particular sport is not exclusive to a particular sport class.

The sport classification 456 is a classification of a sport. In an exemplary embodiment, the sport classification 456 is similar in concept to the sport classification 404 previously discussed with respect to FIG. 4A. The position classification 458 is a classification of a particular position associated with a particular sport. In an exemplary embodiment, the position class 458 is similar in concept to the position 410 previously discussed with respect to FIG. 4A.

In yet an additional exemplary embodiment, an athlete, a training coach, a recruiter, etc., may select an evaluation level to which data is compared. For example, a high school baseball player may select an evaluation level associated with professional baseball. In this example, if a sports tree that is similar to the sports tree 450 of FIG. 4b. is utilized to identify a peer group to which the data is to be compared, the high school baseball player may then be compared to other small target dynamic sports at a similar competition level rather than being compared to baseball players at a higher competition level. Therefore, it may be advantageous in an embodiment for the high school baseball player to select an evaluation level that differs from that which is provided by a sports tree function. It is understood that in an exemplary embodiment any evaluation level may be selected to which sensory data is compared. For example, sensory data of a college target non-dynamic sport may be compared to a professional or youth competition level large-target dynamic evaluation group. Therefore, while a sports tree function is provided to identify an evaluation level, manual or semi-manual selection of an evaluation level is also contemplated.

Returning to FIG. 2, the evaluation level identifying device 216 may use the sports tree functions 218 to identify one or more evaluation levels to associate with a subject. In an exemplary embodiment, the evaluation level identifying device 216 determines if peer data associated with a particular evaluation level is statistically powerful. If the peer data is determined not to be statistically powerful, the evaluation level identifying device 216 may then identify another evaluation level associated with the subject. The sports tree functions 218 may include a plurality of functions that are used alone or in combination to identify an evaluation level for a subject.

The data analyzer 220 analyzes data. In an exemplary embodiment, the data analyzer 220 analyzes a subject's sensory data relative to peer sensory data. For example, a subject's sensory data may include a skill test result for the subject's contrast sensitivity. The contrast sensitivity of the subject is then analyzed along with peer data to identify a percentile ranking of the subject relative to the peer data. Therefore, the subjects contrast sensitivity may be quantitatively compared to a group of similar subjects.

The assessment generator 222 generates an assessment. In an embodiment of the present invention, an assessment is a comparative profile. Similarly, a comparative profile, in an embodiment, is an example of an assessment. Therefore, the assessment generator 222 may generate a comparative profile for use by the training program developer 224. In an exemplary embodiment, the assessment generator generates an assessment of a subject's analyzed sensory data. For example, a graphical output that charts the percentile ranking of a subject's various skill tests may be generated to facilitate understanding of the subject's sensory abilities. In particular, such an assessment may provide context to the subject's sensory ability results through the relative comparisons of peer data.

The training program developer 224 develops a training program. In an exemplary embodiment, the training program developer develops a training program for a subject utilizing the assessment generated by the assessment generator 222 and the data analysis of the data analyzer 220. A training program is a program that may refine and/or improve a subject's sensory ability through training. For example, sensitivity, endurance, shift, quickness, perception, coordination, timing, and equilibrium are examples of sensory activities that may be improved with training. Therefore, a sensory training program may identify one or more sensory related activities that could benefit from training.

The training program developer 224, in an exemplary embodiment, utilizes the training program functions 226 to develop a training program. The training program functions 226 are one or more functions that may be used to identify sensory skills that are to be targeted for training.

For example, turning to FIG. 5A that illustrates a dynamic sports training program function 500 in accordance with an exemplary embodiment of the present invention. The dynamic sports training program function 500 includes an order column 502, a skill test column 504, a first percentile range 506 column, a second percentile 508 column, a third percentile 510 column, and a fourth percentile 512 column. Further, the dynamic sports training program function 500 includes skill tests associated with a first class 522 and skill tests associated with a second class 524. The dynamic sports training function 500 may be implemented for a user who has been classified as being associated with a dynamic sport. For example, with reference to the sports tree function 450 of FIG. 4B, a dynamic sport may include those associated with the small target dynamic classification 460, the large target dynamic classification 462, and the non-target dynamic classification 466 (e.g., hockey, baseball, tennis, basketball, American football, global football, boxing, and snowboarding). The dynamic sports training program function 500 may include one or more skill tests that may not be included with a non-dynamic sports training program function, as will be discussed with respect to FIG. 5B.

The ordered column 502 orders the skill tests. In this example, fifteen skill tests are included in this exemplary dynamic sports training program function 500. The skill test column 504 includes skill test 1 514, skill test 8 516, skill test 9 518, and skill test 15 520. In this example, skill test 1 514 and skill test 8 516 are associated with the first class 522. Further, in this example, skill test 9 518 and the skill test 15 520 are associated with the second class. As a result of the four percentile ranges and the two classes, eight portions are generated. A first portion 526 comprises an area defined by class 522 and percentile range 506. A second portion 528 comprises an area defined by class 522 and percentile range 508. A third portion 530 comprises an area defined by the class 524 and the percentile range 506. A fourth portion 532 comprises an area defined by the class 524 and the percentile range 508. A fifth portion 534 comprises an area defined by the class 522 and the percentile range 510. A sixth portion 536 comprises an area defined by the class 524 and the percentile range 510. A seventh portion 538 comprises an area defined by the class 522 and the percentile range 512. An eighth portion 540 comprises an area defined by the class 524 and the percentile range 512. While the dynamic sports training program function 500 merely includes two class and four percentile ranges, it is contemplated additional or fewer class and/or percentile ranges may be utilized in order to facilitate the generation of a training program. For example, additional percentile ranges may be employed to provide a higher level of control when determining skill tests to include in a training program. Additionally, it is contemplated that any number of skill tests may be associated with the first class 522 and/or the second class 524. Therefore, while a particular number of skill tests are illustrated within FIG. 5A, variations are contemplated.

In an exemplary embodiment, the first percentile range 506 includes skill tests that are in the approximate range of 1% to 24% relative to a selected peer data set. In an exemplary embodiment, the second percentile range 508 includes skill tests that are in the approximate range of 25% to 49%. In an exemplary embodiment, the third percentile range 510 includes skill tests that are in the approximate range of 50% to 74%. In an exemplary embodiment, the fourth percentile range 512 includes skill tests that are in the approximate range of 75% to 99%.

In yet an additional exemplary embodiment, the first class 522 may include the following skill tests: static visual acuity, a contrast sensitivity, a dynamic visual acuity, a visual endurance, a near dynamic shift, a near-far quickness, a fixation disparity, and a depth perception. An exemplary embodiment arranges the skill tests in the order provided above. For example, the skill test 1 514 is the static visual acuity skill test and the skill test 8 516 is the depth perception skill test. However, it is understood that the skill tests of the first class 522 are not limited in scope nor order to the skill tests described herein. The second class 524, in an exemplary embodiment, may include the following skill tests, which may be in the following order: speed/span of perception, reaction time, eye-hand coordination, go no-go, split attention, anticipation timing, and visual equilibrium. The second class 524 is not limited in scope to the skill tests identified herein.

As previously discussed, depending on the subject, the evaluation level, and other factors, additional, different, or fewer skill tests may be used for that subject. For example, a middle school softball player may not be tested or trained using the same skill test as a professional football player. This may be a factor of the different evaluation levels (e.g., sports class, sport, competition level, position class, position) for each of the subjects.

Additional factors may be implemented into a training program function. For example, it may be desirable to have at least one training skill test from a particular class. In particular, an exemplary embodiment ensures that at least one skill test from a second class (e.g., second class 524) is included with a training program. Therefore, depending on the training program algorithm, if a specified number of skill tests are defined to be included in a training program, then a skill test from a second class substitutes a skill test from a first class. This maintains the defined number of skill tests while satisfying a criterion of having at least one skill test from a second class. It is contemplated that additional skill tests may be included in a training program to satisfy a condition. Further, it is contemplated that conditions of the training program may include requiring skill tests within a certain percentile range to have priority in being included in a training program.

Turning to FIG. 5B that illustrates a non-dynamic sports training program function 550 in accordance with an exemplary embodiment of the present invention. In an exemplary embodiment, the non-dynamic sports training program function 550 may be similar in concept to the dynamic sports training program function 500 previously discussed at FIG. 5A. However, in an exemplary embodiment, one or more skill tests that may be included in the dynamic sport training program function 500 may not be included in the non-dynamic sports training program function 550. For example, a first class 552 may include skill tests that are directed to static sensory tests and the second class 554 may include skill tests that are directed to dynamic sensory tests. In an exemplary embodiment, a go no-go skill test and a reaction time skill test may not be included in non-dynamic sports training program function 550. Furthermore, it is contemplated herein that the ordering of one or more skill tests may deviate from an order of a dynamic training program to a non-dynamic training program. For example, while the first class 522 and the second class 524 of FIG. 5A may be categorized by non-dynamic (e.g., static) and dynamic skill tests, the first class 552 and the second class 554 may utilize a different categorization or no particular categorization at all. As a result, while a division between a first and a second class may be illustrated based on categorization, it is contemplated that a categorization is not used to define skill tests for one or more classes.

In an exemplary embodiment, a user who is associated with a non-dynamic sport, such as the target non-dynamic classification 464 discussed previously with respect to FIG. 4B may benefit from the non-dynamic sports training program function 550. For example, because one or more dynamic skill tests may not be performed on a given user, a different sports training program function may be employed to develop a sports training program. It is contemplated that various sports training program functions may be utilized depending on testing and/or training devices, equipment, and procedures available for a particular user. For example, a particular training facility may not have or allow all sensory training activities prescribed when a particular sports training program function is employed; therefore, an alternative sports training program function may be implemented to result in a sports training program that includes available equipment, devices, techniques, or the like.

Figure 6:
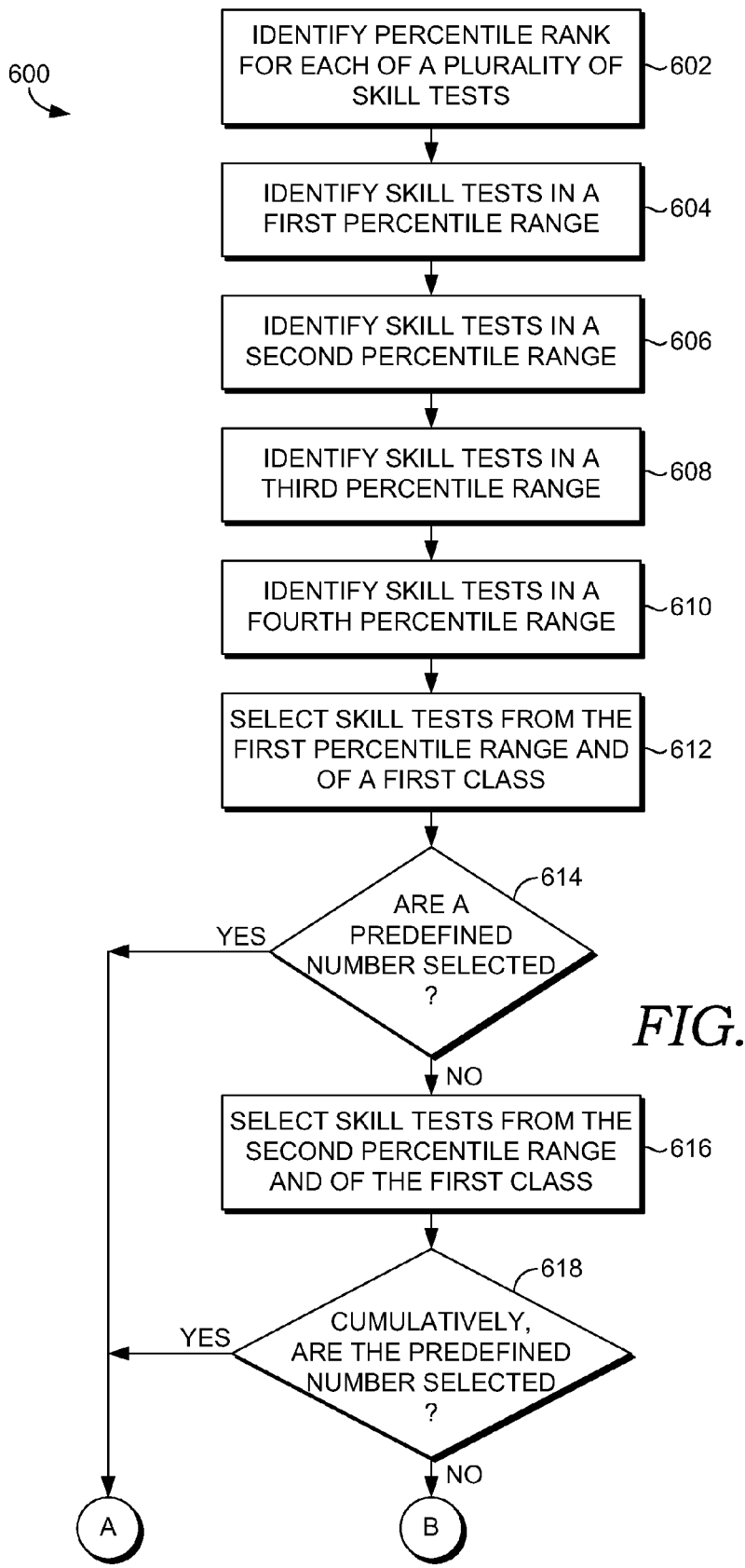
FIG. 6 illustrates a training program function flow diagram in accordance with an exemplary embodiment of the present invention.
Figure 6:
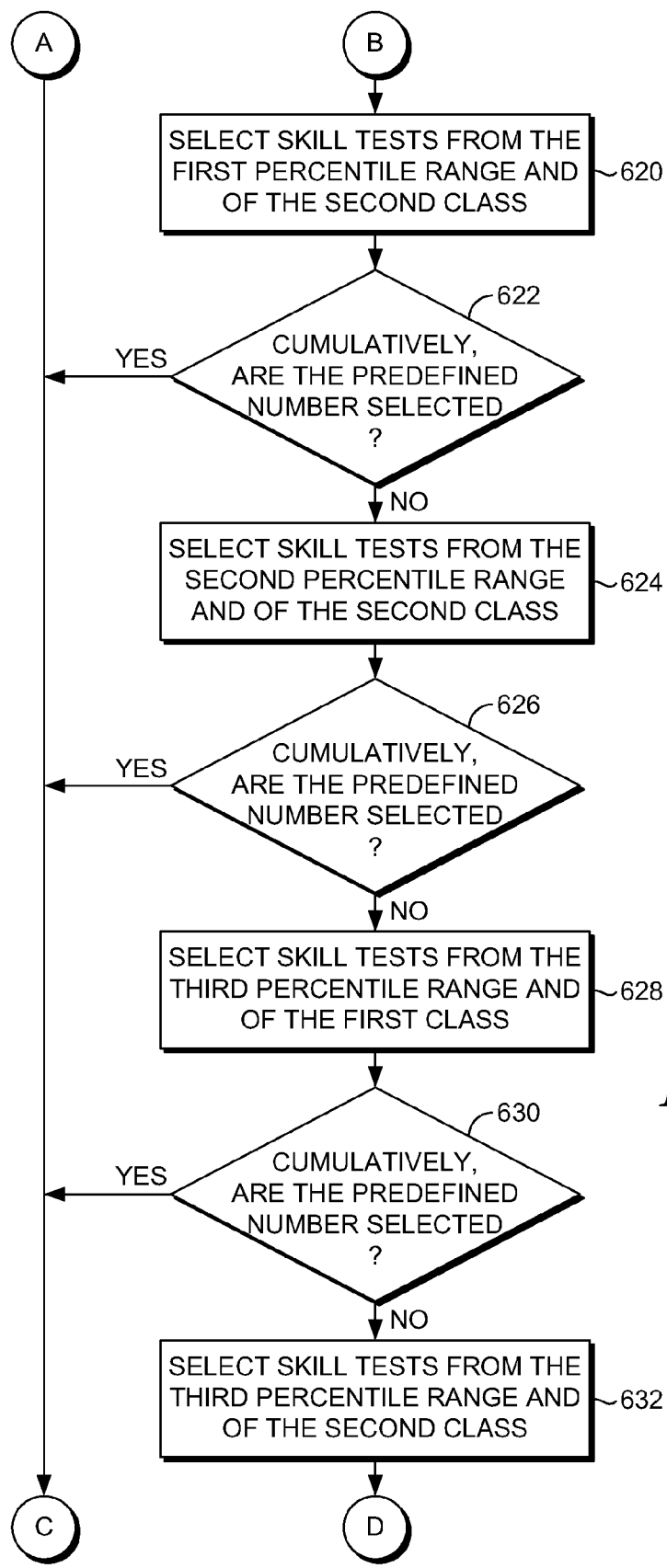
Figure 6:
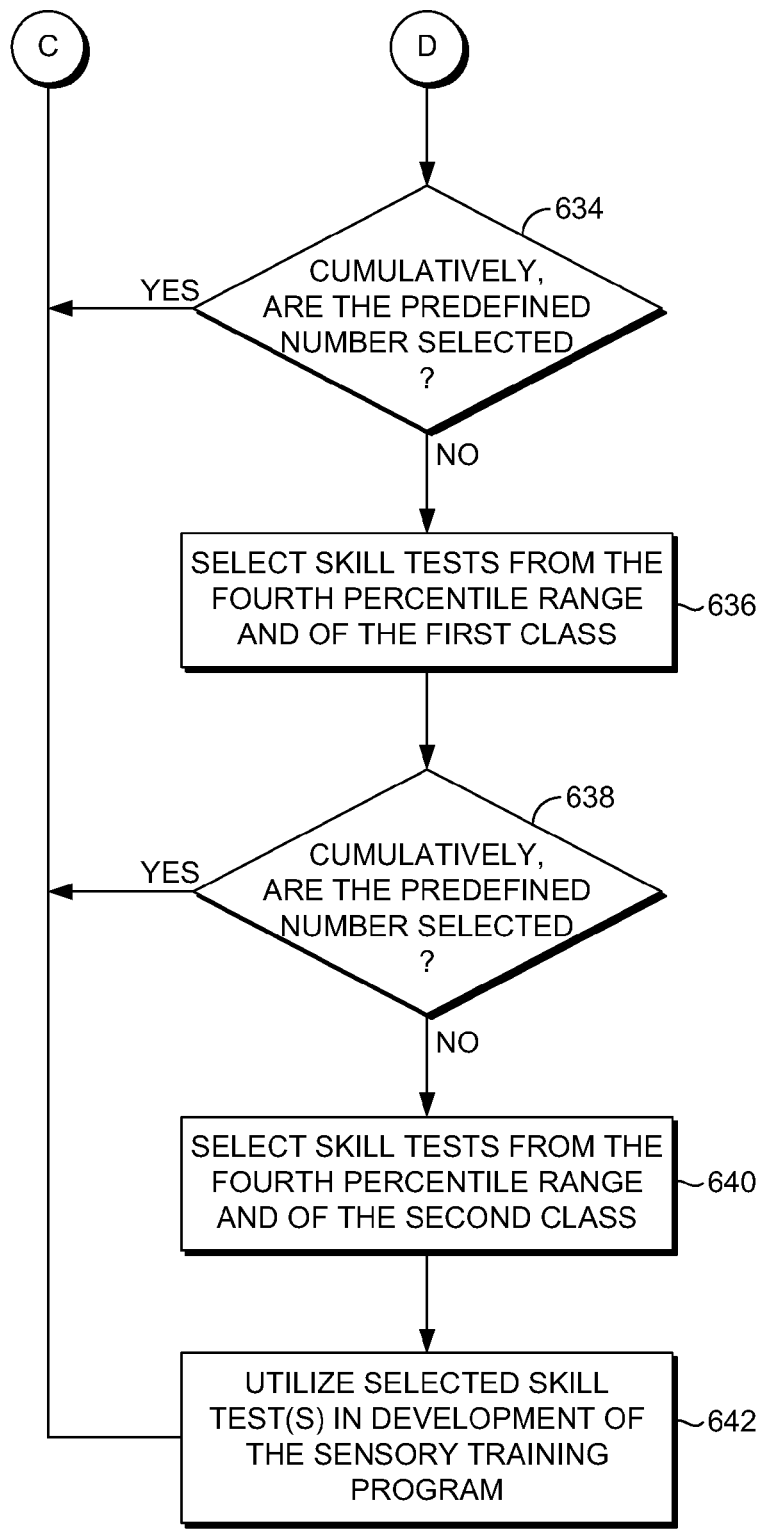

Turning to FIG. 6 that illustrates a training program function 600 flow diagram in accordance with an exemplary embodiment of the present invention. At a block 602, a percentile rank for each of a plurality of skill tests are identified. For example, if sensory data associated with a subject includes the subject's contrast sensitivity results, when analyzed relative to statistically powerful peer data, it is identified that the subject has contrast sensitivity results that are at the twenty-third percentile range. Therefore, this indicates that 77% of peer subjects that are included in the subject's evaluation level have superior results for contrast sensitivity. The identification of percentile ranks may continue for all skill tests to be evaluated by the training program function 600.

At a block 604, skill tests (i.e., one or more skill tests) are identified in a first percentile range. For example, if the first percentile range includes those skill tests that rank from 1% to 24% relative to peer data, then those skill tests identified at block 602 with a percentile rank that is within the first percentile range are identified as being included in the first percentile range. Using the example above, the subject's contrast sensitivity that was identified as being at a 23% ranking may be identified as being included in the first percentile range because it falls between the 1% and 24% range. To further illustrate this point; in this example, the contrast sensitivity would be included in the percentile range 506 of the FIG. 5A.

At a block 606, skill tests are identified in a second percentile range. For example, the second percentile range may include skill tests that are ranked from 25% to 49% relative to peer data. Therefore, skill tests previously identified as having a rank within the second percentile range are now identified being included in the second percentile range. This effectively sorts the various skill tests into their appropriate percentile ranges. At a block 608, skill tests are identified in a third percentile range. For example, the third percentile range may include skill tests that are ranked from 50% to 74% relative to peer data. At a block 610, skill tests are identified in a fourth percentile range. For example, the fourth percentile range may include skill tests that are ranked from 75% to 99% relative to peer data. As a result, skill tests are associated with an appropriate percentile range. It is contemplated, as previously discussed, that additional percentile ranges may be used in order to adjust the level of detail from which a training program is developed. Additionally, in an exemplary embodiment, the one or more percentile ranges, when viewed as a whole, includes all possible percentile rankings of all possible skill tests. Further, while percentile rankings are discussed in the exemplary embodiment as a method of categorizing results, it is contemplated to utilize additional measures for classifying and grouping one or more skill test results. For example, the raw data score of a skill test may be utilized rather than relying on a percentile adjustment.

The training program function 600 continues at a block 612. At the block 612, skill tests from the first percentile range and of a first class are selected. For example, skill tests classified in the first portion 526 of FIG. 5A are selected. Therefore, in an exemplary embodiment, a skill test that is classified as a first class and also identified as being included in a first percentile range is selected for inclusion in a training program. In an exemplary embodiment, the skill tests that satisfy the conditions (e.g., class, percentile range) are selected in a descending order according to an associated skill test order (e.g., according to associated order of an order column such as order column 502 of FIG. 5A). Further, an additional exemplary embodiment includes limiting the number of selected skill tests based on a predefined number. For example, the number of selected skill tests may be limited to four skill tests, six skill tests, eight skill tests, etc. In such an embodiment where the number of skill tests is limited to a predefined number, the order in which they are selected may alter a resulting training plan. In yet a further embodiment, a predefined number of tests selected from one or more classes may be limited or required. For example, at least one skill test from a second class may be required in an exemplary embodiment. As used herein, the selection of a skill test represents the selection of one or more sensory abilities that are measured by the selected skill test. Therefore, in an exemplary embodiment, the selection of a skill test referred to as contrast sensitivity signifies that a subject's contrast sensitivity (e.g., a particular sensory ability) has been selected to be trained, as opposed to indicating that the particular skill test has been selected. In an embodiment, the contrast sensitivity may be trained using the contrast sensitivity test that has been selected, or an additional activity (e.g., test) may be used to train the subject's contrast sensitivity sensory ability. For example, if a particular skill tests is effective for testing a subjects particular sensory ability but not as effective for training, the selected skill test may not be the skill test that is ultimately used to train the related sensory ability.

The training program function 600 continues at a block 614. At the block 614, a determination is made if a predefined number of skill tests have been selected. For example, the training program function may be limited to selecting four skill tests in total from all potential ranges and class combinations. Therefore, the determination is performed to determine if the predefined number of selectable skill tests have been selected. In this example, if the predefined number of skill tests have been selected then the training program function advances at a block 642. As a result, additional skill tests are not selected from one or more combinations of classes and percentile ranges.

However, if the determination at block 614 determines the predefined number of skill tests are not selected (e.g., the number of skill tests that are included in the first percentile range and the first class are less than the predefined number), the training program function advances to a block 616. At the block 616, skill tests from a second percentile range and of the first class are selected. For example, skill tests located within the second portion 528 of FIG. 5A may be selected in an exemplary embodiment, as the second portion 528 of FIG. 5A is comprised of the area defined by a first class and a second percentile range. Upon the selection indicated at the block 616, the training program function 600 advances to a block 618.

The block 618 includes a determination if the predefined numbers of skill tests have been cumulatively selected. For example, if the predefined number is once again four skill tests and three skill tests were previously selected at the block 612, if one additional skill is selected at block 616, then the cumulative number of selected skill tests selected equals the predefined number. If the determination at block 618 determines the predefined number of skill tests have been selected, the training program function 600 advances to the block 642. In the alternative, if the determination does not determine that the number of selected skills tests does not cumulatively equal or exceed the predefined number, then the training program function may proceed to a block 620.

In an exemplary embodiment the number of skill tests identified—and therefore potentially selected—with a given percentile rank and class may exceed the predefined number. Therefore, skill tests may be selected in the order in which they are arranged (e.g., based upon the order column 502 of FIG. 5A). For example, if the skill test 1 514 of FIG. 5A and skill tests 8 516 are both identified with the second portion 528 and only one skill test is needed to equal a predefined cumulative number of skill tests, then the skill test 1 514 may be selected while the skill test 8 516 is not selected based on their relative order to one another. As a result, in an exemplary embodiment, a determination as to if the number of selected skill tests exceeds the predefined number is performed after each selection of a skill test.

At the block 620, skill tests from the first percentile range and of a second class are selected. For example, skill tests identified in the third portion 530 of FIG. 5A may be selected at the block 620. At a block 622, a determination is performed to determine if the cumulative number of selected skill tests equals or exceeds the predefined number of skill tests to be selected. The determination at block 622 may be similar to the determination previously discussed with respect to block 618. When the predefined number of skill tests have not been selected, the training program function 600 advances to a block 624. At block 624 skill tests identified with the second percentile range and of the second class are selected. For example, skill tests identified with the fourth portion 532 of FIG. 5A may be selected at the block 624. At a block 626, a determination is performed to determine if the cumulative number of selected skill tests equals or exceeds the predefined number of skill tests to be selected. At a block 628, skill tests from a third percentile range and the first class are selected. For example, skill tests identified with the fifth portion 534 of FIG. 5A may be selected at block 628. At a block 630, a determination is performed to determine if the cumulative number of selected skill tests equals or exceeds the predefined number of skill tests to be selected. At a block 632, skill tests from the third percentile range and the second class are selected. For example, skill tests identified with the sixth portion 536 of FIG. 5A may be selected at the block 632. At a block 634, a determination is performed to determine if the cumulative number of selected skill tests equals or exceeds the predefined number of skill tests to be selected. At a block 636, skill tests from a fourth percentile range and the first class are selected. For example, skill tests identified with the seventh portion 538 of FIG. 5A may be selected at the block 636. At a block 638, a determination is performed to determine if the cumulative number of selected skill tests equals or exceeds the predefined number of skill tests to be selected. At a block 640, skill tests from the fourth percentile range and the second class are selected. For example, skill tests identified with the eighth portion 540 of FIG. 5A may be selected at the block 640.

At the block 642, the one or more selected skills are utilized in the development of the sensory training program. For example, if four sensory skills have been selected by the sensory training function 600, such as static visual acuity, contrast sensitivity, visual endurance, and anticipation timing, a sensory training program is generated that includes activities directed to training sensory skills associated with the selected skill tests. Therefore, in an exemplary embodiment, a training program may prescribe a static visual acuity training exercise, a contrast sensitivity training exercise, a visual endurance training exercise, and an anticipation timing training exercise. In yet an additional exemplary embodiment, a referral to a practitioner (e.g., optometrist) may also be provided as part of the development of the sensory training program. For example, if a subject's visual acuity is below a predefined threshold, the subject may not even be provided a complete sensory training program as a result of one or more sensory abilities falling below one or more thresholds. In this example, the subject may be referred to a practitioner to correct one or more deficiencies prior to qualifying for a sensory training program. In an exemplary embodiment, a training exercise includes characteristics similar to the sensory skill test that was selected. Alternatively, the training exercise may intentionally avoid including characteristics of the sensory test to prevent the subject from learning the test rather than training a particular sensory ability.

Returning to FIG. 2 and in particular to the remote location 206. The remote location 206 is comprised of a testing device 230, a data transfer device 232, a data collection device 234, an assessment presentation device 236, and a sensory training program presentation device 238.

The testing device 230 may include any device capable of testing or measuring sensory ability. A test administrator may collect the testing data provided by the testing device 230 in an electronic format and may store the collected testing data to a computing device located at the remote location 206, the central location 202, or an alternative location coupled to the network 204. Once this occurs, the data transfer device 232 may transfer the testing data, via any suitable method depending on the format of the data, to the central location 202. The data transfer device 232 may be any device that can transfer data, such as a modem, network card, and the like.

The testing device 230 may create the data resulting from the sensory ability tests administered to a subject or any other sensory ability measurements. In this embodiment, the data collection device 234 may collect the data provided by testing device 230. By way of example, and not limitation, data collection device 234 may be any device that includes solid-state memory, hard drives, flash memory, and the like. Further, as discussed above, the data collection device 234 may collect the data from the testing device 230, either directly or indirectly. That is, an individual may directly input data from the testing device 230 into the data collection device 234. Alternatively, the devices may work together to directly collect the data.

The assessment presentation device 236 is a device functional to present an assessment. For example, the assessment presentation device 236 may include a display for visually presenting the assessment. In an exemplary embodiment, the assessment presentation device is comprised of a screen capable of outputting an assessment generated by the assessment generator 222. In a further embodiment, the assessment presentation device 236 provides additional or alternative methods of presenting an assessment. For example, printing capabilities, audible output, electronic presentation (e.g., formatted presentation for a mobile device or Internet capable device). Similarly, the sensory training program presentation device 238 is a device functional to present a sensory training program. In an exemplary embodiment, the sensory training program presentation device 238 presents a sensory training program developed by the training program developer 224 and communicated by the assessment and training program communicator 228.

Figure 7:
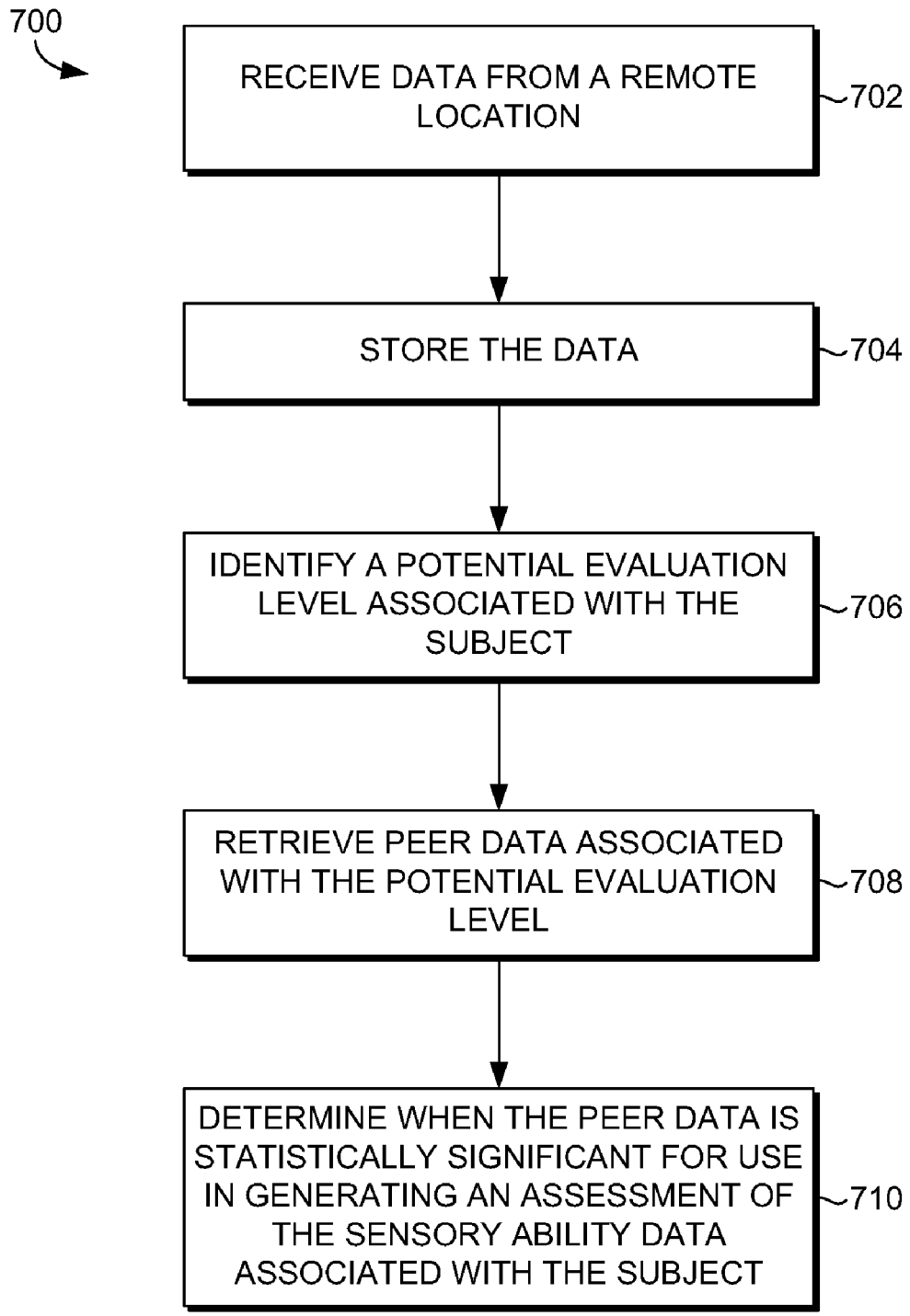
FIG. 7 illustrates a block diagram depicting a method of analyzing sensory ability data at a central location utilizing a computing device having memory and a processor in accordance with an embodiment of the present invention.

Turning to FIG. 7 that depicts a method 700 of analyzing sensory ability data at a central location utilizing a computing device having memory and a processor in accordance with an embodiment of the present invention. At a step 702, data is received from a remote location. For example, sensory data, demographic data, and remote location data may be communicated from a remote location to a central location where it is received to be stored and analyzed. In an exemplary embodiment, the data is "pushed" from the remote location. Data is pushed when it has not been requested by the receiving entity, such as the central location. In an alternative embodiment, the data is "pulled" from the remote location. Data may be pulled when it is requested by the intended recipient. Additionally, the data may be received by a combination of pushing and pulling. For example, a remote location may push an indication that data is available to be pulled from the remote location.

At a step 704, the data received is stored. In an exemplary embodiment, the data is stored in one or more computer readable media, such as a data store. Further, the data received may be separated into multiple data types. For example, if the data comprises two or more of sensory data, demographic data, and remote information, then each of those types of data may be stored in a particular location as defined by a data structure. Additionally, if the data is separated by a defined data structure, an association or key (e.g., primary and secondary keys) may be utilized to define an association among the separated data. The association may facilitate analysis and recall at a later time. As previously discussed, the data may be stored in a data store directly coupled to the central location, indirectly coupled with the central location (e.g., coupled by way of a network connection), or a combination of the two.

At a step 706, a potential evaluation level is identified as being associated with a subject. In an exemplary embodiment, the received data is associated with a particular test subject and the data is used to identify an associated evaluation level. For example, the demographic data of the subject may be used in connection with a sports tree function to identify a potential evaluation level. An identified evaluation level may be referred to as a potential evaluation level because peer data associated with the potential evaluation level has not been verified to be statistically powerful. Therefore, while an evaluation level may be identified initially, because of a predefined statistical power requirement, the evaluation level may be amended to achieve the desired level of statistical power. In an exemplary embodiment, the evaluation level is preferred to be at the finest level of detail (e.g., at the position level of an exemplary sports tree), but when peer data at that level is determined to not be statistically powerful, the evaluation level may be amended to a broader level (e.g., at the position class level of an exemplary sports tree) that may include statistically powerful data.

At a block 708, peer data associated with the potential evaluation level is retrieved. For example, a computing device of a central location may retrieve, from a data store, peer data associated with the potential evaluation level. In an exemplary embodiment, a plurality of subjects' data is stored in a data store accessible by a data analyzer. The subjects' data may include sensory data and demographic data associated with each of the subjects. As a result, the subjects' data serves as a peer data pool to which the received data may be analyzed. In an effort to provide valuable analysis, it may be beneficial to limit the pool of peer data to only that which is associated with a similar evaluation level.

At a step 710, a determination is made to determine when the peer data is statistically powerful for use in generating a comparative profile of the sensory ability data associated with the subject. In an exemplary embodiment, the determination is made by a data analyzer. For example, the data analyzer may analyze the peer data to determine if the peer data satisfies a predefined condition to be statistically powerful. As previously discussed, data is determined statistically powerful when a condition is satisfied. For example, a predefined number of data points may be required before the data is determined to be statistically powerful. A particular statistical value (e.g., p-value) may need to be achieved before the data is considered to be statistically powerful. In an exemplary embodiment, statistical power is determined to maintain a level of quality associated with any resulting assessments and sensory training programs.

Figure 8:
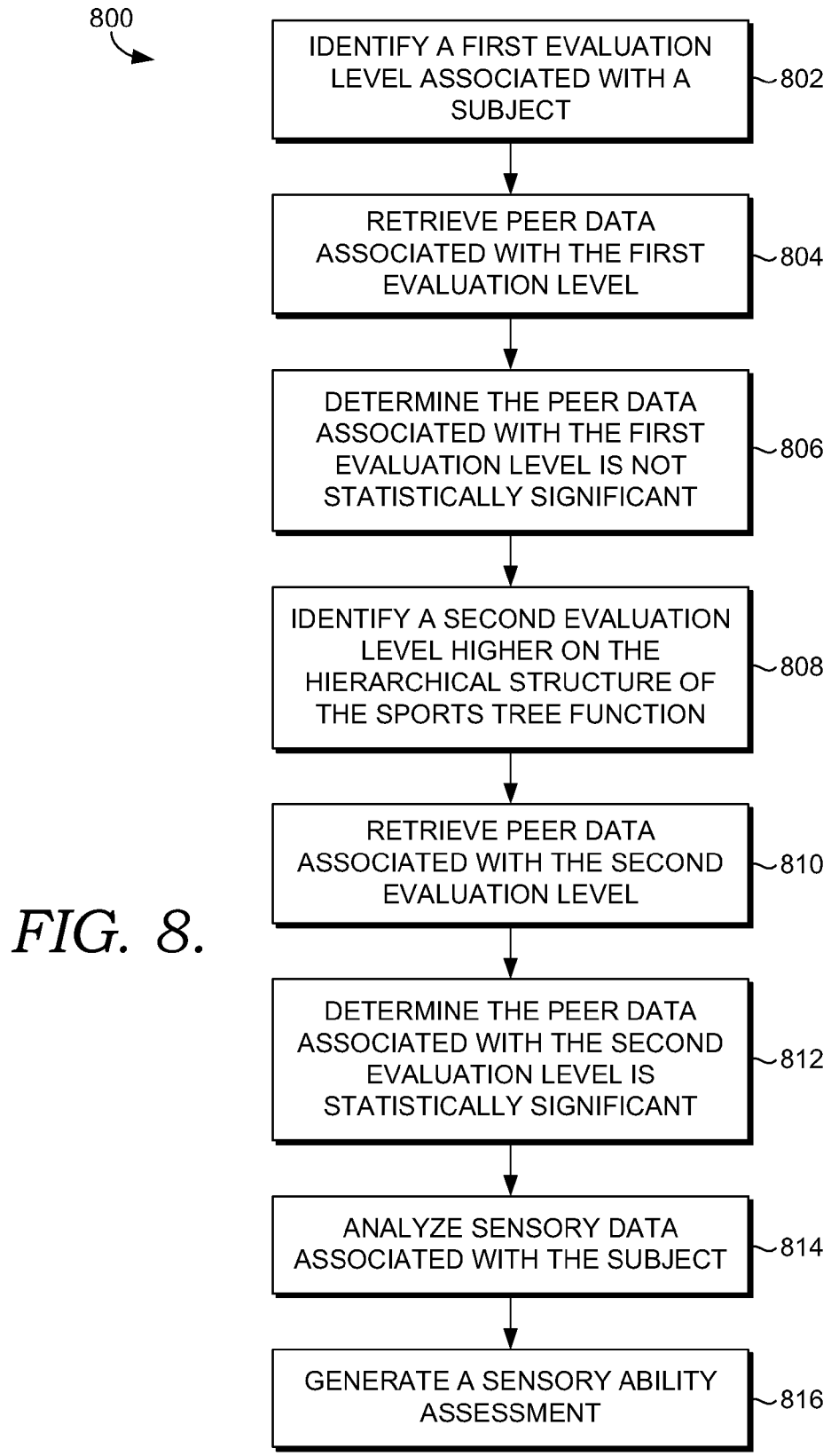
FIG. 8 illustrates a block diagram depicting a method for analyzing sensory ability data of a subject in accordance with an exemplary embodiment of the present invention.

Turning to FIG. 8 that depicts a method 800 for analyzing sensory ability data of a subject in accordance with an exemplary embodiment of the present invention. At a step 802, a first evaluation level associated with a subject is identified. As previously discussed, an evaluation level may be identified by an evaluation level identifying device using a sports tree function. For example, demographic data of a subject may be used in combination with a sports tree function to identify a group of peers sharing a common evaluation level.

At a step 804, peer data associated with the first evaluation level is retrieved. For example, if the first evaluation level is identified as including a high school football quarterback, then data of other high school football quarterbacks is retrieved. In an exemplary embodiment, the data is retrieved from a data store that includes a relational database for retrieving and identifying data associated with a similar evaluation level. At a step 806, the peer data associated with the first evaluation level is determined to not be statistically powerful. For example, a data analyzer may analyze the peer data and determine that a predefined condition for statistical power has not been satisfied.

At a step 808, a second evaluation level, which is higher on a hierarchical structure of a sports tree function, is identified. For example, if the first evaluation level included a particular position, the second evaluation level may be broadened to only include the position class. Therefore, the second evaluation level is higher in an exemplary sports tree function. Once again, in an exemplary embodiment, the second evaluation level may be determined by an evaluation level identifying device using a sports tree function.

At a step 810, peer data associated with the second evaluation level is retrieved. Similar to step 804, the data may be retrieved from a data store accessible by one or more computing devices. At a step 812, the peer data associated with the second evaluation level is determined to be statistically powerful. For example, the same criteria used at step 806 may once again be employed to determine the statistical power of the data. In an additional embodiment, a different condition may be defined for the second evaluation level to ensure that a quality assessment and training program may result with the broader evaluation level.

At a step 814, the sensory data associated with the subject is analyzed. In an exemplary embodiment, the sensory data is analyzed by a data analyzer. The data analyzer may compare the subject's sensory data to the peer data associated with a selected evaluation level. For example, the data analyzer may analyze the subject's sensory data at each of the data skill tests included with the sensory data relative to the peer data associated with the second evaluation level. Therefore, the data analyzer may identify a percentile rank for each of the subject's skill tests relative to a group of peers. For example, if 70% of the peers have static visual acuity results that are greater than the subject, the data analyzer may identify the subject is in the thirtieth percentile for static acuity. Further, if 20% of the peers have split attention results that are greater than the subject, then the data analyzer may identify that the subject is in the eightieth percentile for split attention skills. The analysis of the subject's data may include analyzing each skill test included with the sensory data, analyzing a specified selection of skill tests associated with the sensory data, and/or analyzing a skill test included in the sensory data. Further, the analysis of data may include analyzing multiple instances of sensory data associated with the subject. For example, if more than one instance of sensory data is stored (e.g., a first testing and a second testing) then all instances may be analyzed to provide temporal change information.

At a step 816, a sensory ability assessment is generated. A sensory ability assessment may include a graphical representation of results derived at the step 814. For example, a chart may be generated that visually represents the subject's sensory abilities relative to peer data. In an exemplary embodiment, the assessment is a line graph that charts the subject's sensory ability percentile relative to a predefined goal at each skill test. A sensory ability assessment may also be a collection of data that is stored and/or provided to the subject, an administrator, and a training program developer. Therefore, in an exemplary embodiment, the generation of a sensory ability assessment results in a physical transformation of the analyzed data into a form useable by one or more entities.

Figure 9:
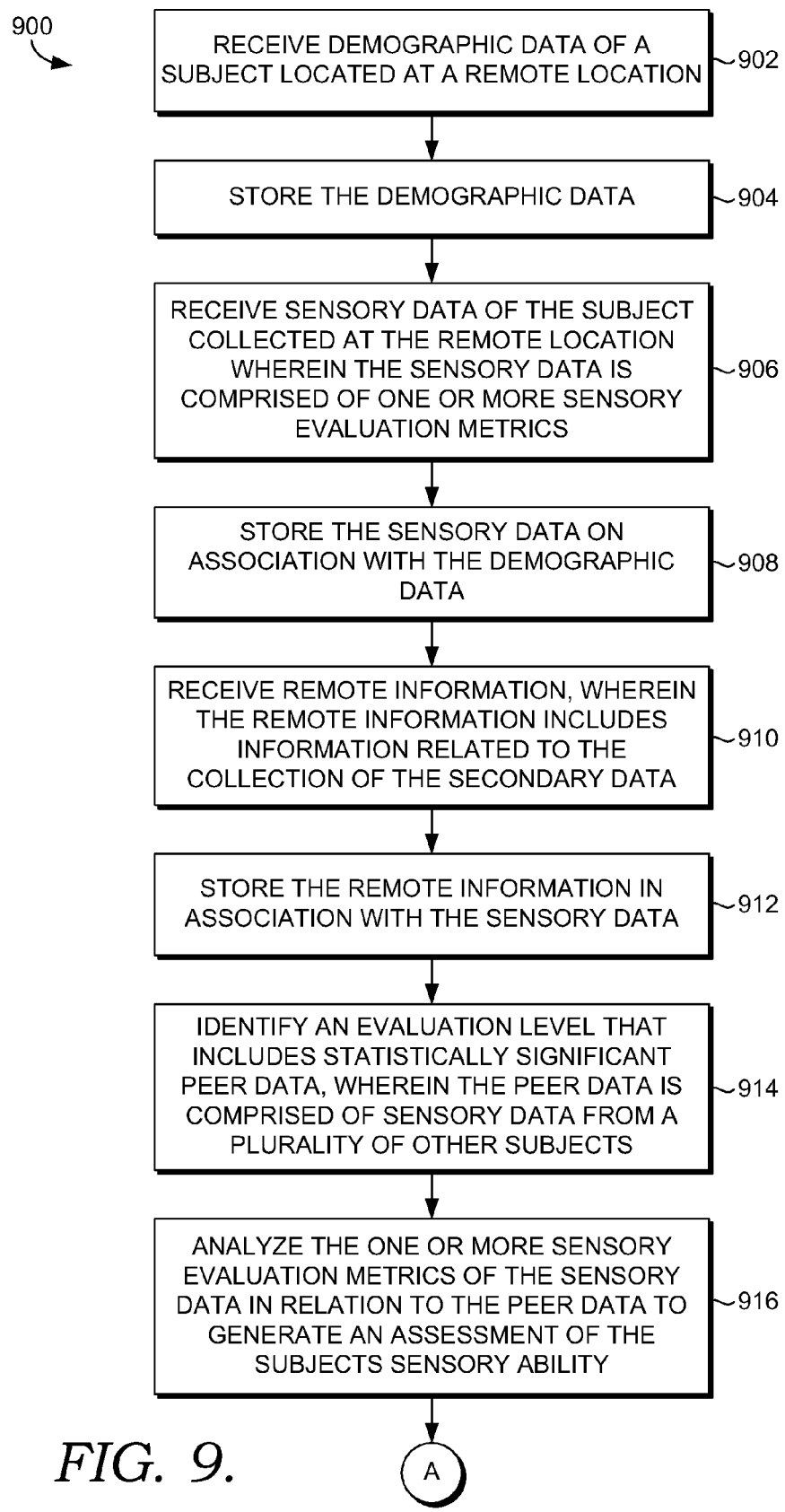
FIG. 9 illustrates a block diagram depicting a method for analyzing sensory ability data of a subject in accordance with an exemplary embodiment of the present invention.
Figure 9:
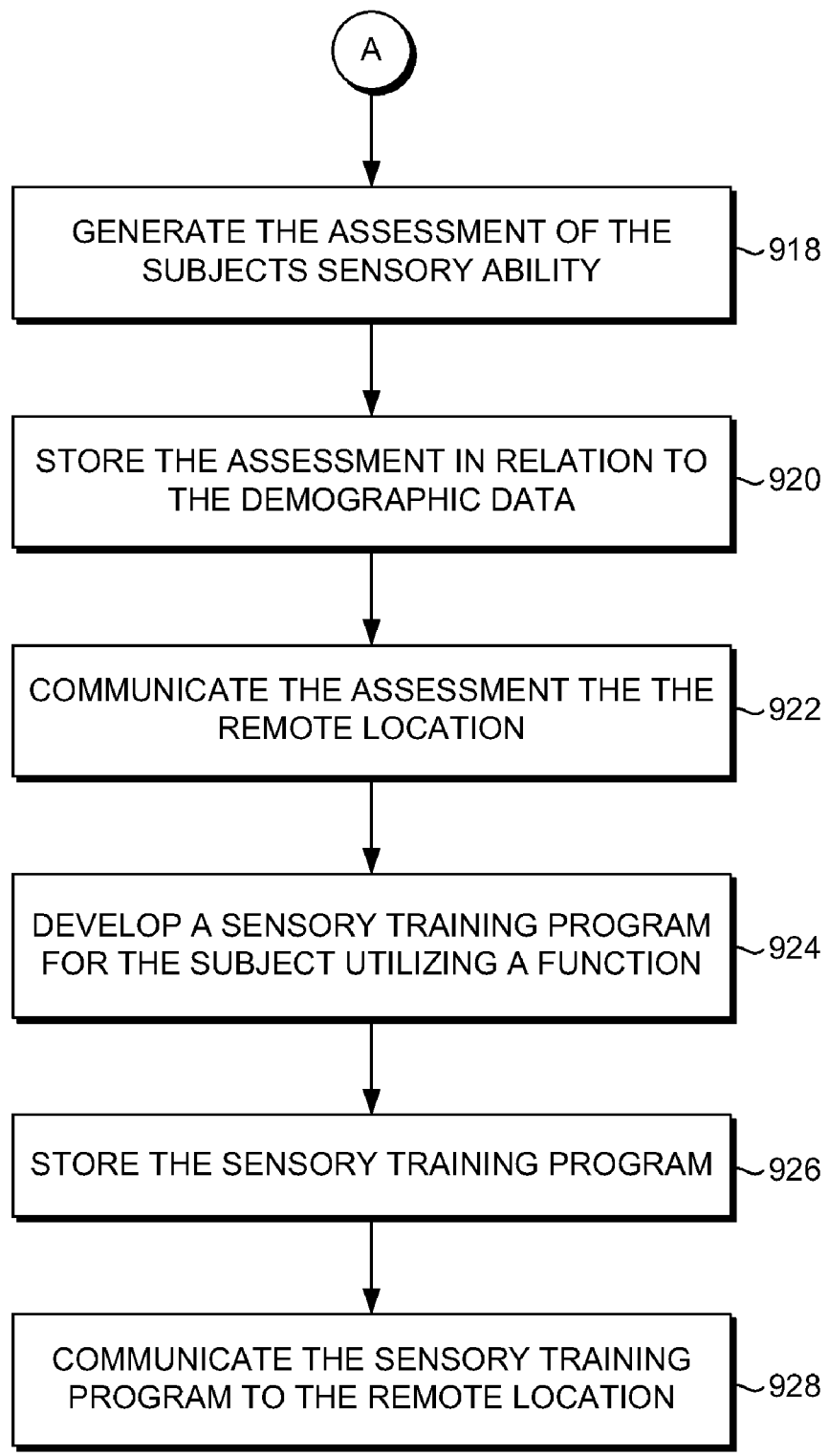

Turning to FIG. 9 that depicts a method 900 for analyzing sensory ability data of a subject in accordance with an exemplary embodiment of the present invention. It is understood that the method 900 may be performed at a remote location, a central location, or a combination of one or more remote locations and central locations. At a step 902, demographic data of a subject that has been collected at a remote location are received. For example, information related to the subject's height, weight, position, competition level, etc., may comprise the demographic data. At a step 904, the demographic data is stored. In an exemplary embodiment, the demographic data is stored at a data store. At a step 906, sensory data of the subject collected at the remote location is received. The sensory data is comprised of one or more sensory evaluation metrics. A sensory evaluation metric is a measurement of a particular sensory ability. Therefore, each sensory skill may have a unique sensory evaluation metric that describes the subject's sensory ability at a particular sensory skill The sensory data may include sensory evaluation metrics for each sensory skill test performed on the subject. At a step 908, the sensory data is stored in association with the demographic data. For example, the sensory data may be stored in a physically or conceptually different location from the demographic data of the subject, but an association is drawn between the two data sets. In an exemplary embodiment, the association is provided by a database key that allows for multiple sets of data to be related to one another.

At a step 910, remote information is received. The remote information includes information related to the collection of the sensory data. For example, the remote information may include an identifier of the testing apparatus, the testing administrator, the remote location, time, date, and the like. At a step 912, the remote information is stored in association with the sensory data. Therefore, information related to the collection of sensory data may be referenced based on the association. For example, if one or more sensory evaluation metrics falls outside of a statistical range and is therefore identified as potentially inaccurate, the remote information may aid in identifying a point of entry for the inaccuracy.

At a step 914, an evaluation level that includes statistically powerful peer data is identified. The peer data is comprised of sensory data from a plurality of other subjects. In an exemplary embodiment, the demographic data is used along with a sports tree function to aid in identifying an appropriate evaluation level for a particular subject. The peer data, as previously discussed, may include one or more subjects' data where the subjects are associated with a similar evaluation level as the current subject. At a step 916, the one or more sensory evaluation metrics of the sensory data are analyzed in relation to the peer data. The analysis is used to generate a comparative profile of the subject's sensory ability. For example, the sensory metrics of the sensory data may indicate a quantitative measurement of the subject's sensory ability at each of the sensory skills included in the sensory data. Therefore, each of the sensory metrics may be analyzed relative to similar sensory metrics from the peer data. Static visual acuity metrics of the subject may be analyzed relative to the static visual acuity metrics included in the peer data.

At a step 918, the assessment of the subject's sensory ability is generated. For example, the generation of an assessment includes formatting the results of the analyzed sensory evaluation metrics into a format useable by the subject, a testing administrator, a trainer, or a training program developer. At a step 920, the assessment is stored in relation to the demographic data. For example, in an embodiment, the assessment is stored in a data store so that it may be retrieved based on demographic data of the subject (e.g., name, identifier, key, birth date). Therefore, the assessment may be located at a later time for comparison or additional analysis and review. At a step 922, the assessment is communicated to the remote location. In an exemplary embodiment, the assessment is stored in a data store that is separate from the remote location; therefore, the assessment may be communicated from the data store to the remote location. In an additional embodiment, the assessment is stored at a data store associated with the remote location, but the assessment is communicated to a presentation device of the remote location.

At a step 924, a sensory training program is developed for the subject utilizing a function. For example, a training program developer may implement one or more training program functions to identify one or more sensory skills to include in a training program for the subject. In an exemplary embodiment, the function evaluates the analyzed skill evaluation metrics to identify those sensory skills in a first class at a first percentile range, then sensory skills in the first class at a second percentile range, followed by sensory skills in a second class at the first percentile range, then sensory skills in the second class and in the second percentile range. The function continues to identify those sensory skills in a third percentile range and then a fourth percentile range. Additionally, the function may include one or more conditions. For example, a condition of the function may require that at least one of the sensory functions included in a training plan are from a particular class. An additional exemplary embodiment includes a condition of the function that limits the number of selected sensory skills to a predefined number. Further, a condition of the function may require a particular sensory skill to be selected (e.g., a sensory skill that is entertaining for the subject to train in order to maintain the subject's interest).

At a step 926, the sensory training program is stored. For example, the sensory training program may be stored at a data store associated with a central location, at a data store associated with the remote location, or at an alternative location. In an exemplary embodiment, the sensory training program is stored in association with the demographic data of the subject. At a step 928, the sensory training program is communicated to the remote location. In an exemplary embodiment, the communication of the sensory training program to the remote location includes communicating the sensory training program to one or more remote locations. The communication of the sensory training program may occur by way of a network connection.

Various methods have been described herein; it is contemplated that one or more of the methods may be implemented in a computing environment by one or more computing devices having processors and memory. Therefore, while certain methods were not discussed with respect to a computing environment, the methods may additionally be implemented in a computing environment using one or more computing devices.

The present invention has been described herein in relation to particular embodiments, which are intended in all respects to be illustrative rather than restrictive.

From the foregoing, it will be seen that this invention is one well-adapted to attain the ends and objects set forth above, together with other advantages that are obvious and inherent to the methods. It will be understood that certain features and subcombinations are of utility and may be employed without reference to other features and subcombinations. This is contemplated by and within the scope of the claims.

The invention claimed is:

1. A method of analyzing sensory ability data at a central location utilizing a computing device having memory and a processor, the method comprising:
   receiving data from a remote location, wherein the data is comprised of sensory ability data and demographic data associated with a subject;
   storing the data;
   identifying a potential evaluation level associated with the subject, wherein the evaluation level is identified, at least in part, utilizing a sports tree function;
   retrieving peer data associated with the potential evaluation level; and
   determining when the peer data is statistically powerful for use in generating a comparative profile of the sensory ability data associated with the subject.

2. The method of claim 1 further comprising:
   analyzing the sensory ability data associated with the subject to generate a sensory ability assessment; and
   generating the sensory ability assessment.

3. The method of claim 2 further comprising:
   developing a sensory training program, wherein the sensory training program is based, at least in part on the sensory ability assessment.

4. The method of claim 3, wherein developing the sensory training program comprises:
   identifying a percentile rank for each of a plurality of skill tests reported with the sensory ability data, wherein each of the skill tests are classified as either a first class or a second class;
   identifying each of the plurality of skill tests in a first percentile range;
   identifying each of the plurality of skill tests in a second percentile range;
   identifying each of the plurality of skill tests in a third percentile range;
   identifying each of the plurality of skill tests in a fourth percentile range; and
   selecting a predefined number of skill tests in the following evaluation order until a total number of selected skill tests equals the predefined number, the evaluation order includes:
   (1) skill tests classified as the first class and associated with the first percentile range,
   (2) skill tests classified as the first class and associated with the second percentile range,
   (3) skill tests classified as the second class and associated with the first percentile range,
   (4) skill tests classified as the second class and associated with the second percentile range,
   (5) skill tests classified as the first class and associated with the third percentile range,
   (6) skill tests classified as the second class and associated with the second percentile range,
   (7) skill tests classified as the first class and associated with the fourth percentile range, and
   (8) skill tests classified as the second class and associated with the fourth percentile range.

5. The method of claim 4 further comprising:
   determining the selected skill tests only include skill tests classified as the first class; and
   including a skill test classified as the second class.

6. The method of claim 4 further comprising:
   determining the selected skill tests only include skill tests classified as the first class; and
   substituting a skill test classified as the second class for a selected skill test classified as the first class.

7. The method of claim 1, wherein the peer data is statistically powerful when the peer data includes a predefined number of data points for use in generating the assessment of the sensory ability data associated with the subject.

8. The method of claim 1 further comprising:
   determining the peer data is not statistically powerful for use in generating a comparative profile of the sensory ability data associated with the subject;
   identifying a broader evaluation level associated with the subject, wherein the broader evaluation level is identified, at least in part, utilizing the sports tree function;
   retrieving peer data associated with the broader evaluation level; and
   determining the peer data associated with the broader evaluation level is statistically powerful for use in generating a comparative profile of the sensory ability data associated with the subject.

9. The method of claim 1 wherein the data is further comprised of remote information.

10. One or more computer-readable media having computer-executable instructions embodied thereon for performing a method for analyzing sensory ability data of a subject, the method comprising:
   identifying a first evaluation level associated with the subject, wherein the evaluation level is identified, at least in part, utilizing a sports tree function, wherein the sports tree function is comprised of a hierarchical structure that represents potential evaluation levels based on one or more traits of the subject;
   retrieving peer data associated with the first evaluation level;
   determining the peer data associated with the first evaluation level is not statistically powerful for use in generating a comparative profile of the sensory ability data associated with the subject;
   identifying a second evaluation level utilizing the sports tree function, wherein the second evaluation level is higher on the hierarchical structure of the sports tree function;
   retrieving peer data associated with the second evaluation level;
   determining the peer data associated with the second evaluation level is statistically powerful for use in generating a comparative profile of the sensory ability data associated with the subject;
   analyzing sensory data associated with the subject to generate a sensory ability assessment; and
   generating the sensory ability assessment.

11. The media of claim 10, wherein the hierarchical structure of the sports tree function is comprised of the following levels: a sport class, a sport, a competition level, a position class, and a position.

12. The media of claim 10, wherein the peer data associated with the second evaluation level comprises personal traits that are broader in scope than personal traits of the peer data associated with the first evaluation level.

13. The media of claim 10 further comprising:
   developing a sensory training program, wherein the sensory training program is based, at least in part on the sensory ability assessment.

14. The media of claim 13 further comprising:
   storing the sensory ability assessment in association with the subject;
   storing the sensory training program in association with the subject;
   presenting the sensory ability assessment; and
   presenting the sensory training program.

15. The media of claim 10, wherein determining the peer data associated with the first evaluation level is not statistically powerful for use in generating a comparative profile of the sensory ability data associated with the subject is done automatically.

16. The media of claim 10, wherein retrieving peer data is comprised of:
   accessing a data store that includes data associated with a plurality of subjects;
   identifying one or more of the plurality of subjects associated with a particular evaluation level; and
   retrieving data associated with the one or more of the plurality of subjects associated with the particular evaluation level.

17. A method for analyzing sensory ability data of a subject, the method comprising:
   receiving demographic data of the subject;
   storing the demographic data;
   receiving sensory data of the subject, the sensory data is collected at a remote location, wherein the sensory data is comprised of one or more sensory evaluation metrics;
   storing the sensory data in association with the demographic data;
   receiving remote information, wherein the remote information includes information related to the collection of the sensory data;
   storing the remote information in association with the sensory data;
   identifying an evaluation level that includes statistically powerful peer data, wherein the peer data is comprised of sensory data from a plurality of other subjects;
   analyzing the one or more sensory evaluation metrics of the subject's sensory data in relation to the peer data to generate a comparative profile of the subject's sensory ability;
   generating the assessment of the subject's sensory ability;
   storing the assessment in association with the demographic data;
   communicating the assessment to the remote location;
   developing a sensory training program for the subject utilizing a training program function;
   storing the training program in association with the demographic data; and
   communicating the sensory training program to the remote location.

18. The method of claim 17, wherein the training program function is comprised of:
   classifying each of the sensory evaluation metrics of the subject's sensory ability data as either a first class or a second class, wherein the sensory evaluation metrics represent a quantitative assessment of a sensory ability;
   identifying a percentile rank for each of the sensory evaluation metrics relative to the peer data; and
   selecting a predefined number of the sensory evaluation metrics, wherein the sensory evaluation metrics are selected in the following order until the predefined number of sensory evaluation metrics have been selected:
   1) select sensory evaluation metrics that are classified as the first class and have an identified percentile rank in a range from 1% to 24%,
   2) select sensory evaluation metrics that are classified as the first class and have an identified percentile rank in a range from 25% to 49%,
   3) select sensory evaluation metrics that are classified as the second class and have an identified percentile rank in the range from 1% to 24%,
   4) select sensory evaluation metrics that are classified as the second class and have an identified percentile rank in a range from 25% to 49%,
   5) select sensory evaluation metrics that are classified as the first class and have an identified percentile rank in a range from 50% to 74%,
   6) select sensory evaluation metrics that are classified as the second class and have an identified percentile rank in a range from 50% to 74%,
   7) select sensory evaluation metrics that are classified as the first class and have an identified percentile rank in a range from 75% to 99%, and
   8) select sensory evaluation metrics that are classified as the second class and have an identified percentile rank in a range from 75% to 99%.

19. The method of claim 18, wherein the training program function is further comprised of:
  identifying the selected sensory evaluation metrics are all classified as the first class; and
  substituting one of the selected sensory evaluation metrics with a sensory evaluation metric classified as the second class.

20. The method of claim 17, wherein the demographic data includes one or more traits of the subject, and wherein the remote information includes one or more identifying characteristics of the remote location.

* * * * *